US011615883B2

(12) United States Patent
Watson et al.

(10) Patent No.: US 11,615,883 B2
(45) Date of Patent: Mar. 28, 2023

(54) PATIENT TRANSPORT AND TRIAGE

(71) Applicant: Cheyenne Mountain Software, LLC, Wichita, KS (US)

(72) Inventors: Richard L. Watson, Wichita, KS (US); Martin E. Sellberg, Wichita, KS (US)

(73) Assignee: Cheyenne Mountain Software, LLC, Wichita, KS (US)

( * ) Notice: Subject to any disclaimer, the term of this patent is extended or adjusted under 35 U.S.C. 154(b) by 0 days.

(21) Appl. No.: 16/377,008

(22) Filed: Apr. 5, 2019

(65) Prior Publication Data

US 2019/0311799 A1 Oct. 10, 2019

Related U.S. Application Data

(60) Provisional application No. 62/653,349, filed on Apr. 5, 2018.

(51) Int. Cl.
  *G16H 40/20* (2018.01)
  *G16H 40/60* (2018.01)
  *G06Q 10/06* (2012.01)
  *G06Q 10/04* (2012.01)
  *G06Q 10/0631* (2023.01)

(52) U.S. Cl.
  CPC ............ *G16H 40/20* (2018.01); *G06Q 10/04* (2013.01); *G16H 40/60* (2018.01); *G06Q 10/0631* (2013.01)

(58) Field of Classification Search
  CPC ........ G16H 40/20; G16H 40/60; G06Q 10/04; G06Q 10/0631
  See application file for complete search history.

(56) References Cited

U.S. PATENT DOCUMENTS

| 6,117,073 A * | 9/2000 | Jones ............... G16H 40/20 600/300 |
| 2001/0044732 A1* | 11/2001 | Maus ............... G06Q 10/10 705/3 |
| 2006/0211404 A1* | 9/2006 | Cromp ............... G06Q 10/10 455/405 |
| 2008/0243549 A1* | 10/2008 | Woronka ............... G16H 15/00 705/3 |
| 2009/0198733 A1* | 8/2009 | Gounares ............... G16H 40/20 |

(Continued)

*Primary Examiner* — Robert W Morgan
*Assistant Examiner* — Chance L Smith
(74) *Attorney, Agent, or Firm* — Davis Wright Tremaine LLP

(57) ABSTRACT

Provided are patient transport and triage methods for use with a mission control computing device configured to execute and implement one or more application modules, and in operative communication over a network with a sender computing device and a dispatch computing device each operable to display one or more dashboards and/or input screens, and with one or more static or dynamic mission control datasets. The networked methods provide a technical solution for improving patient transport and triage by providing, confirming and sharing patient acuity and transport information among multiple relevant parties at the same time to provide better patient outcomes. Also provided are systems for implementing the methods, and computer readable media having stored thereon computer-executable instructions for performing the methods.

53 Claims, 17 Drawing Sheets

(56) References Cited

U.S. PATENT DOCUMENTS

| | | | | |
|---|---|---|---|---|
| 2013/0065628 | A1* | 3/2013 | Pfeffer | G08B 25/016 |
| | | | | 455/521 |
| 2013/0246960 | A1* | 9/2013 | Saylors | G16H 15/00 |
| | | | | 715/771 |
| 2014/0249850 | A1* | 9/2014 | Woodson | G16H 10/60 |
| | | | | 705/3 |
| 2016/0098930 | A1* | 4/2016 | Dillingham | G08G 5/0021 |
| | | | | 715/772 |
| 2016/0140299 | A1* | 5/2016 | Al Harbi | G06F 19/00 |
| | | | | 705/2 |
| 2017/0344707 | A1* | 11/2017 | Patel | G08G 1/202 |
| 2017/0345114 | A1* | 11/2017 | Brandt | G06Q 10/02 |
| 2019/0159009 | A1* | 5/2019 | Barash | G08B 25/016 |
| 2019/0214129 | A1* | 7/2019 | Radhakrishnan | D06F 43/00 |

* cited by examiner

LEVEL OF CARE — 214

Do they have a time critical illness? e.g., stroke, acute MI, trauma, sepsis

What is the care they will need?

In the previous 2 hours, have serious symptoms needed treatment such as hemodynamic instability, arrhythmia, intractable pain, or other?

SUPPORT — 216

Does their blood pressure or heart rhythm require control, either by drips or pacing?
Are they receiving blood products or have they just completed receiving blood products?
Is respiratory support necessary through invasive or noninvasive means?

RISK OF DETERIORATION

Are they early in their critical course requiring transfer, i.e. 2h or less in the hospital?

Would ground transport put them out of the hospital environment for more than 45 minutes?

| | ORIGIN | DESTINATION | ACUITY | CURRENT LEG | STATUS |
|---|---|---|---|---|---|
| M1 | Dodge City → 104 | Wichita → 106 | 3 → 226 | 0 of 1 — Weather along path | PENDING |
| | | VFR | | Active since Thu Mar 22 2018 20:36:19 GMT+00:00 (PST) | |
| M2 | Hastings | Wichita | 11 | 2 of 3 | accepted | missions — 146

Legs show the current crew and the status of the leg. When a leg is checked "COMPLETE", the next leg (if any) is shown. If the leg is checked "CANCELED" the mission is canceled and stored to be referenced later missions drop down "on select" and reveal details of the mission.

plus button is a way to create a mission outside of the acuity calculator and is only accessible by dispatch

FIG. 11A

PATIENT TRANSPORT AND TRIAGE

CROSS-REFERENCE TO RELATED APPLICATION

This application claims the benefit of U.S. Provisional Patent Application No. 62/653,349, filed Apr. 5, 2018, the disclosure of which is herein incorporated by reference in its entirety.

BACKGROUND OF THE INVENTION

Field of the Invention

The present invention is directed generally to methods and systems for transporting and triaging human patients.

Description of the Related Art

Presently, transferring a patient from a first location (e.g., a first hospital) to a second location (e.g., a second hospital) requires a number of different telephone calls because all of the connections between the relevant parties are made via the telephone. Further, each of the relevant parties has no knowledge of what any of the other parties are doing and has no specific knowledge with regard to the condition of the patient. Thus, there is no adequate way to triage the patient. Further, patient information cannot be confirmed with two or more of the relevant parties at the same time.

SUMMARY OF PARTICULAR ASPECTS OF THE INVENTION

Provided are triaged patient transport methods for use with a mission control computing device configured to execute and implement one or more application modules, and in operative communication over a network with a sender computing device and a dispatch computing device each operable to display one or more dashboards and/or input screens, and with one or more static or dynamic mission control datasets, the method comprising: receiving, by an acuity module (AM), inputted patient and transportation information from the sender computing device, and generating by the AM a patient acuity score and a patient transport plan, wherein the transport plan comprises a sending location, a receiving location, a mode of transportation, and a level of crew specialization, and wherein the acuity score is matched, independently or in unison, with the transportation mode, the crew specialization level, and the appropriate receiving station; receiving, by a transport request module (TRM), the acuity score and the transport plan, generating by the TRM a transport request that includes the acuity score and the transport plan, updating by the TRM one or more dashboards, including a dispatcher dashboard on the dispatcher computing device at a transport center, with the transport request, and receiving, by the TRM, a receiver (receiving location) acceptance response for the transport request from the dispatch computing device; converting, by a mission planning and tracking module (MPTM), the accepted transport request into a transport mission that assigns an appropriate vehicle to transport the patient, and that optionally assigns one or more crew members having the level of crew specialization specified in the transport plan, receiving by the MPTM a crew acknowledgement, receiving, by the MPTM, an indication that the patient has been picked up for transport, and updating by the MPTM one or more dashboards, including the dispatcher dashboard, to provide a coordinated handshake between the sender, the receiver and the dispatcher to efficiently transfer command and responsibility for the patient from the sending location to the transport center; receiving, by the MPTM, notification from the dispatcher that the patient has been delivered to the receiving station to provide a coordinated handshake between the sender, the receiver and the dispatcher to efficiently transfer command and responsibility for the patient from the transport center to the receiving location; and closing the transport mission by the MPTM.

The methods may further comprise, prior to receiving the inputted patient and transportation information by the acuity application, accessing, over the network, the acuity application using the sender computing device to display the interface providing the one or more input screens for inputting the patient and transportation information. The methods may further comprise, prior to receiving, by the transport request application, the acceptance response from the dispatcher, receiving by the transport request application a rejection response from the dispatcher, and generating by the transport request application the transport request with an alternate receiving station. In the methods, receiving by the MPTM a crew acknowledgement, may comprise updating, by the MPTM, one or more dashboards of a crew computing device connected to the network at a transport base to display the crew assignment, and receiving, by the MPTM, a crew acknowledgement from the crew computing device. The methods may further comprise use of a receiver computing device, at the receiving location, connected to the network and operative to display one or more dashboards and/or input screens, and wherein updating by the MPTM one or more dashboards, may include updating the dispatcher dashboard and a dashboard displayed on the recipient computing device, to provide a coordinated handshake between the sender, the receiver and the dispatcher to efficiently transfer command and responsibility for the patient from the sending location to the transport center. In the methods, the appropriate vehicle and/or the one or more crew members assigned by the MPTM may be initially selected by the dispatcher by inputting this information in a mission input screen displayed on the dispatcher computing device. In the methods, assigning, by the MPTM, the appropriate transport vehicle and optionally assigning the one or more crew members having the level of crew specialization specified in the transport plan, may comprise use of a hard asset deployment module, and optionally a crew assignment module, respectively. In the methods, assigning the transport vehicle by the hard asset deployment module, and optionally assigning the one or more crew members by the crew assignment module, may comprise use of a vehicle profile dataset and a crew profile dataset, respectively, in the methods, assigning the transport vehicle by the hard asset deployment module, and optionally assigning the one or more crew members by the crew assignment module, may comprise use of the vehicle profile dataset and a crew profile dataset to calculate weight, balance and fuel requirements. In the methods, assigning, by the MPTM, the appropriate transport vehicle and optionally assigning the one or more crew members, may comprise use of a weather evaluation module. In the methods, assigning, by the MPTM, the appropriate transport vehicle and optionally assigning the one or more crew members, may comprise consideration/optimization of one or more of resource availability, proximity, efficiency, cost, or reimbursement. In the methods, assigning, by the MPTM, the appropriate transport vehicle and optionally assigning the one or more crew members, may comprise assignment of a vehicle based on comparison of historical transport mission data between or among a plurality of transport bases. In the methods, after transferring command and responsibility for the patient from the sending location to the transport center, and prior to receiving notification from the dispatcher that the patient has been delivered to the receiving station, the position of the transport vehicle may be tracked by the MPTM to provide a vehicle location and an estimated time of arrival. In the methods, during patient transport the MPTM may update one or more dashboards, including the dispatcher dashboard, with changes to the patient's condition based on input from the assigned crew. In the methods, during patient transport the MPTM may update one or more dashboards, including the dispatcher dashboard, with the vehicle location and the estimated time of arrival, and/or may update an accessible vehicle position dataset. In the methods, closing the transport mission by the MPTM, may comprise prior receipt of a close instruction from the sender, the receiver, and/or the dispatcher. The methods may comprise sending, by the MPTM, a mission summary to the sending and/or receiving locations. In the methods, receiving, over the network by the AM, inputted patient and transportation information from the sender computing device, may comprise receiving the patient and the transportation information from the receiver and/or the dispatcher. In the methods, generating the acuity score and/or the transportation plan by the AM and/or converting the accepted transport request into the transport mission by the MPTM may further comprise accessing one or more static or dynamic mission control datasets. In the methods, the mission control data sets may comprise one or more of a diagnosis-based protocol dataset, a vehicle profile dataset, a crew profile dataset, a hospital dataset, a weather dataset, an airport conditions dataset, or a vehicle position dataset. In the methods, the diagnosis-based protocol dataset may comprise predetermined protocols for treating different medical conditions; the vehicle profile dataset may comprise information for one or more of fuel, speed, fuel consumption, or weight limits for each vehicle; the crew profile dataset may comprise weight and/or experience information each of the crew members; the hospital dataset may store information about each hospital that may function as either the sending location or the receiving location; the weather dataset may store information about the current weather; the airport conditions dataset may store the condition of one or more airports that may be used to complete a transport mission; and the vehicle position dataset may store positions of those vehicles currently conducting missions. In the methods, any computing device connected to the network for use in the method may be implemented as a computing device 12 or a mobile communication device 300. Additionally provided is a computer readable medium (e.g., non-transitory) having stored thereon computer-executable instructions for performing the methods.

Additionally provided are transport methods for use with a mission control computing device configured to execute and implement one or more application modules, and in operative communication over a network with a sender computing device and a dispatch computing device each operable to display one or more dashboards and/or input screens, and with one or more static or dynamic mission control datasets, the method comprising: receiving, by a transport request module (TRM), patient and transportation information inputted from the sender computing device and/or from the dispatcher computing device at a transport center, generating by the TRM a transport request that includes an acuity score and a transport plan, wherein the transport plan comprises a sending location, a receiving location, a mode of transportation, and a level of crew specialization, and wherein the acuity score is matched, independently or in unison, with the transportation mode, the crew specialization level, and the appropriate receiving station, updating by the TRM one or more dashboards, including a dispatcher dashboard on the dispatcher computing device, with the transport request, and receiving, by the TRM, a receiver (receiving location) acceptance response for the transport request from the dispatch computing device; converting, by a mission planning and tracking module (MPTM), the accepted transport request into a transport mission that assigns an appropriate vehicle to transport the patient, and that optionally assigns one or more crew members having the level of crew specialization specified in the transport plan, receiving by the MPTM a crew acknowledgement, receiving, by the MPTM, an indication that the patient has been picked up for transport, and updating by the MPTM one or more dashboards, including the dispatcher dashboard, to provide a coordinated handshake between the sender, the receiver and the dispatcher to efficiently transfer command and responsibility for the patient from the sending location to the transport center; receiving, by the MPTM, notification from the dispatcher that the patient has been delivered to the receiving station to provide a coordinated handshake between the sender, the receiver and the dispatcher to efficiently transfer command and responsibility for the patient from the transport center to the receiving location; and closing the transport mission by the MPTM.

The methods may further comprise, prior to receiving the inputted patient and transportation information by the TRM, accessing, over the network, the TRM using the dispatcher computing device to display the interface providing the one or more input screens for inputting the patient and transportation information. The methods may further comprise, prior to receiving, by the TRM, the acceptance response from the dispatcher, receiving by the TRM a rejection response from the dispatcher, and generating by the TRM the transport request with an alternate receiving location. In the methods, receiving by the MPTM a crew acknowledgement, may comprises updating, by the MPTM, one or more dashboards of a crew computing device connected to the network at a transport base to display the crew assignment, and receiving, by the MPTM, a crew acknowledgement from the crew computing device. The methods may further comprise use of a receiver computing device, at the receiving location, connected to the network and operative to display one or more dashboards and/or input screens, and wherein updating by the MPTM one or more dashboards, may include updating the dispatcher dashboard and a dashboard displayed on the recipient computing device, to provide a coordinated handshake between the sender, the receiver and the dispatcher to efficiently transfer command and responsibility for the patient from the sending location to the transport center. In the methods, the appropriate vehicle and/or the one or more crew members assigned by the MPTM may be initially selected by the dispatcher by inputting this information in a mission input screen displayed on the dispatcher computing device. In the methods, assigning, by the MPTM, the appropriate transport vehicle and optionally assigning the one or more crew members having the level of crew specialization specified in the transport plan, may comprise use of a hard asset deployment module, and optionally a crew assignment module, respectively. In the methods, assigning the transport vehicle by the hard asset deployment module, and optionally assigning the one or more crew members by the crew assignment module, may comprise use of a vehicle profile dataset and a crew profile dataset, respectively. In the methods, assigning the transport vehicle by the hard asset deployment module, and optionally assigning the one or more crew members by the crew assignment module, may comprise use of the vehicle profile dataset and a crew profile dataset to calculate weight, balance and fuel requirements. In the methods, assigning, by the MPTM, the appropriate transport vehicle and optionally assigning the one or more crew members, may comprise use of a weather evaluation module. In the methods, assigning, by the MPTM, the appropriate transport vehicle and optionally assigning the one or more crew members, may comprise consideration/optimization of one or more of resource availability, proximity, efficiency, cost, or reimbursement. In the methods, assigning, by the MPTM, the appropriate transport vehicle and optionally assigning the one or more crew members, may comprise assignment of a vehicle based on comparison of historical transport mission data between or among a plurality of transport bases. In the methods, after transferring command and responsibility for the patient from the sending location to the transport center, and prior to receiving notification from the dispatcher that the patient has been delivered to the receiving station, the position of the transport vehicle may be tracked by the MPTM to provide a vehicle location and an estimated time of arrival. In the methods, during patient transport the MPTM may update one or more dashboards, including the dispatcher dashboard, with changes to the patient's condition based on input from the assigned crew. In the methods, during patient transport the MPTM may update one or more dashboards, including the dispatcher dashboard, with the vehicle location and the estimated time of arrival, and/or may update an accessible vehicle position dataset. In the methods, closing the transport mission by the MPTM, may comprise prior receipt of a close instruction from the sender, the receiver, and/or the dispatcher. The methods may comprise sending, by the MPTM, a mission summary to the sending and/or receiving locations. In the methods, receiving, over a network by the TRM, inputted patient and transportation information, may comprise receiving the patient and the transportation information from the receiver and/or the dispatcher. In the methods, generating the transport request by the TRM and/or converting the accepted transport request into the transport mission by the MPTM may further comprise accessing one or more static or dynamic mission control datasets. In the methods, the mission control data sets may comprise one or more of a diagnosis-based protocol dataset, a vehicle profile dataset, a crew profile dataset, a hospital dataset, a weather dataset, an airport conditions dataset, or a vehicle position dataset. In the methods, the diagnosis-based protocol dataset may comprise predetermined protocols for treating different medical conditions; the vehicle profile dataset may comprise information for one or more of fuel, speed, fuel consumption, or weight limits for each vehicle; the crew profile dataset may comprise weight and/or experience information each of the crew members; the hospital dataset may store information about each hospital that may function as either the sending location or the receiving location; the weather dataset may store information about the current weather; the airport conditions dataset may store the condition of one or more airports that may be used to complete a transport mission; and the vehicle position dataset may store positions of those vehicles currently conducting missions. In the methods, any computing device connected to the network for use in the method may be implemented as a computing device 12 or a mobile communication device 300. Additionally provided is a computer readable medium (e.g., non-transitory) having stored thereon computer-executable instructions for performing the methods.

Further provided are systems for triaging patients for transport from a sending location to a receiving location by matching patient acuity with transport and recipient resources over a network, comprising: a sender computing device; a dispatch computing device; one or more static or dynamic mission control datasets stored in memory; a mission control computing device, in operative communication over a network with the sender computing device, the dispatch computing device, and the datasets, and configured to execute and implement one or more application modules, including: an acuity module (AM) operative to: display an interface providing one or more input screens on the sender computing device for inputting patient and transportation information by a sender; receive the inputted patient and transportation information; and generate a patient acuity score and a transportation plan, wherein the transportation plan comprises a sending location, a receiving location, a mode of transportation, and a level of crew specialization, and wherein in generating the transportation plan the acuity score is matched, independently or in unison, with the transportation mode, the level of crew specialization, and the receiving station; a transport request module (TRM) operative to: receive the acuity score and the transport plan from the AM; generate a transport request that includes the acuity score and the transport plan; update one or more dashboards, including a dispatcher dashboard displayed on the dispatch computing device at a transport center, with the transport request; and receive a receiver (receiving location) acceptance response for the transport request from a dispatcher; a mission planning and tracking module (MPTM) operative to: convert the accepted transport request into a transport mission that assigns an appropriate vehicle to transport the patient and optionally assign one or more crew members having the level of crew specialization specified in the transport plan; receive an indication that the patient has been picked up for transport, and update one or more dashboards including the dispatcher dashboard to provide a coordinated handshake between the sender, the receiver and the dispatcher to efficiently transfer command and responsibility for the patient from the sending location to the transport center; to receive notification from the dispatcher that the patient has been delivered to the receiving station to provide a coordinated handshake between the sender, the receiver and the dispatcher to efficiently transfer command and responsibility for the patient from the transport center to the receiving location; and close the transport mission.

The system may further comprise one or more of a receiver computing device, and a crew/base computing device, in each case operatively connected to the network. The systems may further comprise a crew computing device, and wherein the MPTM may be operative to update one or more dashboards of the crew computing device to display the crew assignment, and to receive a crew acknowledgement from the crew computing device. The systems may further comprise a hard asset deployment module, and/or a crew assignment module, and wherein the MPTM may be operative with one or both of said modules in assigning the appropriate transport vehicle and optionally in assigning the one or more crew members. In the systems, the hard asset deployment module and the crew assignment module may be operative to access a vehicle profile dataset and/or a crew profile dataset to calculate one or more of weight, balance, or fuel requirements in assigning the transport vehicle and optionally in assigning the one or more crew members, respectively. The systems may further comprise a weather evaluation module, and wherein the MPTM may be operative to use the weather evaluation module in assigning the appropriate transport vehicle and optionally in assigning the one or more crew members. In the systems, the MPTM may be operative, during patient transport, to track the position of the transport vehicle to provide a vehicle location and an estimated time of arrival, to update one or more dashboards, including the dispatcher dashboard, with the vehicle location and the estimated time of arrival, and/or update an accessible vehicle position dataset, and/or to update one or more dashboards, including the dispatcher dashboard, with changes to the patient's condition based on input from the assigned crew. In the systems, the AM, the MPTM, and/or the TRM may be operative to access the one or more static or dynamic mission control datasets. In the systems, the one or more mission control data sets may comprise one or more of a diagnosis-based protocol dataset, a vehicle profile dataset, a crew profile dataset, a hospital dataset, a weather dataset, an airport conditions dataset, or a vehicle position dataset. In the systems, the diagnosis-based protocol dataset may comprise predetermined protocols for treating different medical conditions; the vehicle profile dataset may comprise information for one or more of fuel, speed, fuel consumption, or weight limits for each vehicle; the crew profile dataset may comprise weight and/or experience information each of the crew members; the hospital dataset may store information about each hospital that may function as either the sending location or the receiving location; the weather dataset may store information about the current weather; the airport conditions dataset may store the condition of one or more airports that may be used to complete a transport mission; and the vehicle position dataset may store positions of those vehicles currently conducting missions. In the systems, any computing device connected to the network for use in the system may be implemented as a computing device 12 or a mobile communication device 300.

BRIEF DESCRIPTION OF THE DRAWINGS

FIG. 4 shows, by way of non-limiting examples of the present invention, an exemplary user input screen 214 including one or more questions related to level of care.

FIG. 5 shows, by way of non-limiting examples of the present invention, an exemplary user input screen 216 including one or more questions related to support.

FIG. 11A shows, by way of non-limiting examples of the present invention, a dispatch dashboard 146 displaying information about missions M1 and M2 involving a transport center 122.

DETAILED DESCRIPTION OF THE INVENTION

Figure 1:
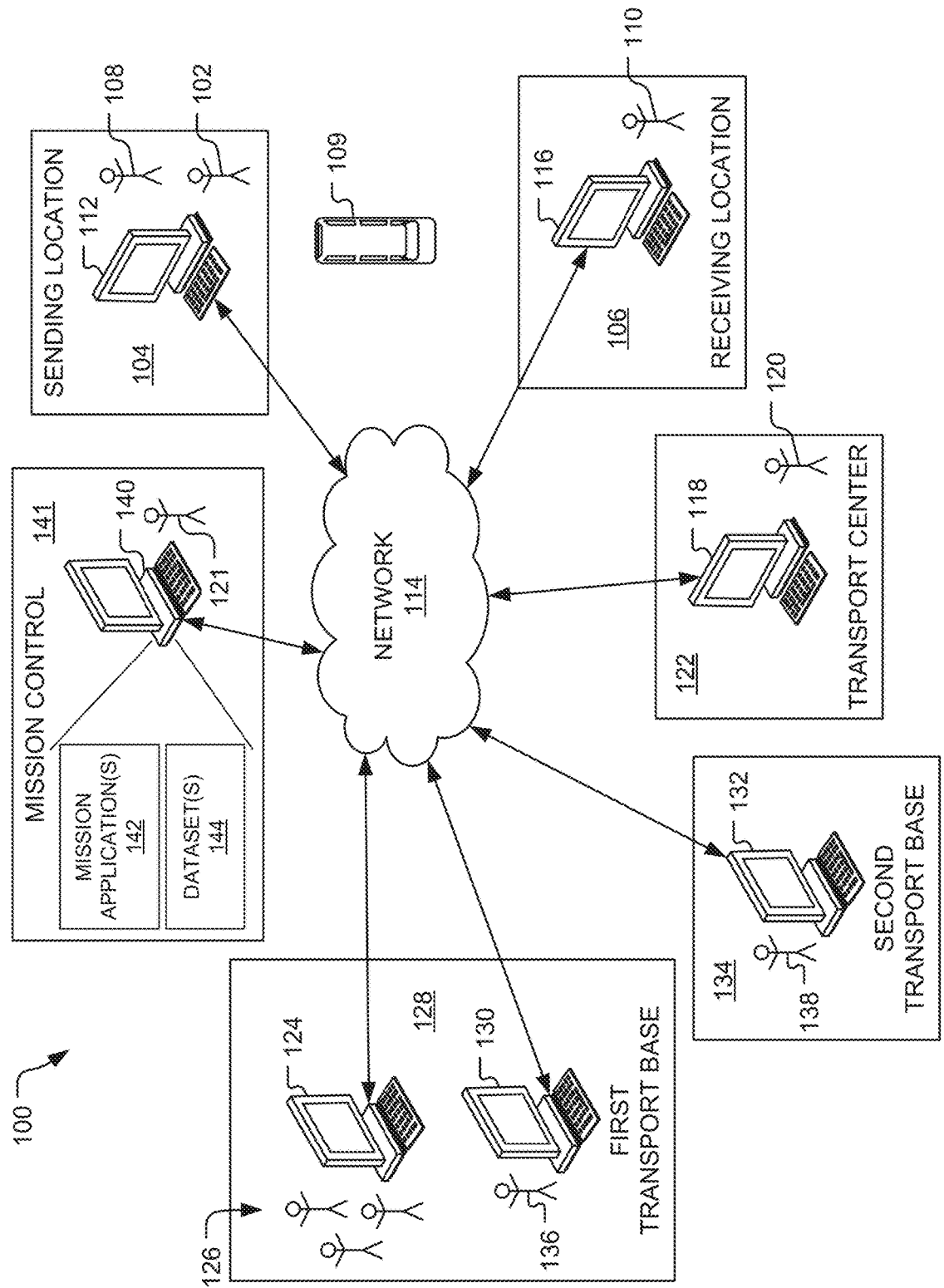
FIG. 1 shows, by way of non-limiting examples of the present invention, a functional block diagram of a system 100 configured to transport a patient 102 from a sending location 104 (e.g., a sending hospital) to a receiving location 106 (e.g., a receiving hospital).

FIG. 1 is a functional block diagram of a system 100 configured to transport a patient 102 from a sending location 104 (e.g., a sending hospital) to a receiving location 106 (e.g., a receiving hospital). As used herein, the term "mission" refers to such a transfer. A sender 108 (e.g., at the sending location 104) requests that the patient 102 be transferred (e.g., via a vehicle 109) from the sending location 104 to the receiving location 106. A receiver 110 (e.g., at the receiving location 106) approves the transfer. By way of non-limiting examples, the sender 108 may be a hospital employee, a first responder, the receiver 110, one or more of a plurality of crew members 126, a dispatcher 120, an employee 121 at a mission control 141, a physician, emergency room personnel, and the like. By way of additional non-limiting examples, the receiver 110 may be a hospital employee, a physician, emergency room personnel, and the like.

The system 100 includes at least one sender computing device 112 operated by the sender 108. The sender computing device 112 may be located at the sending location 104. The sender computing device 112 is connected to a network 114.

Optionally, the system 100 may include at least one receiver computing device 116 operated by the receiver 110. The receiver computing device 116 may be located at the receiving location 106. The receiver computing device 116 is connected to the network 114.

The system 100 includes at least one dispatch computing device 118 operated by the dispatcher 120. The dispatch computing device 118 may be located at a transportation center 122. The dispatch computing device 118 is connected to the network 114.

Optionally, the system 100 may include at least one crew computing device 124 operated by one of the plurality of crew members 126. The crew computing device 124 may be located at a first transport base 128. The crew computing device 124 is connected to the network 114.

Optionally, the system 100 may include a different base computing device for each transport base. In the embodiment illustrated, the system 100 includes base computing devices 130 and 132 for first and second transport bases 128 and 134, respectively. The base computing devices 130 and 132 are operated by people 136 and 138, respectively, tasked with tracking vehicles associated with the first and second transport bases 128 and 134, respectively. The base computing devices 130 and 132 may be located at the first and second transport bases 128 and 134, respectively. The base computing devices 13( ) and 132 are each connected to the network 114.

The system 100 includes at least one mission control computing device 140 connected to the network 114. The mission control computing device(s) 140 may be located at the mission control 141. The mission control computing device(s) 140 execute and implement one or more mission applications 142. The mission control computing device(s) 140 is/are configured to access one or more datasets 144 that may be stored by the mission control computing device(s) 140 or another computing device (not shown) connected to the mission control computing device(s)140 (e.g., by the network 114).

Figure 13:
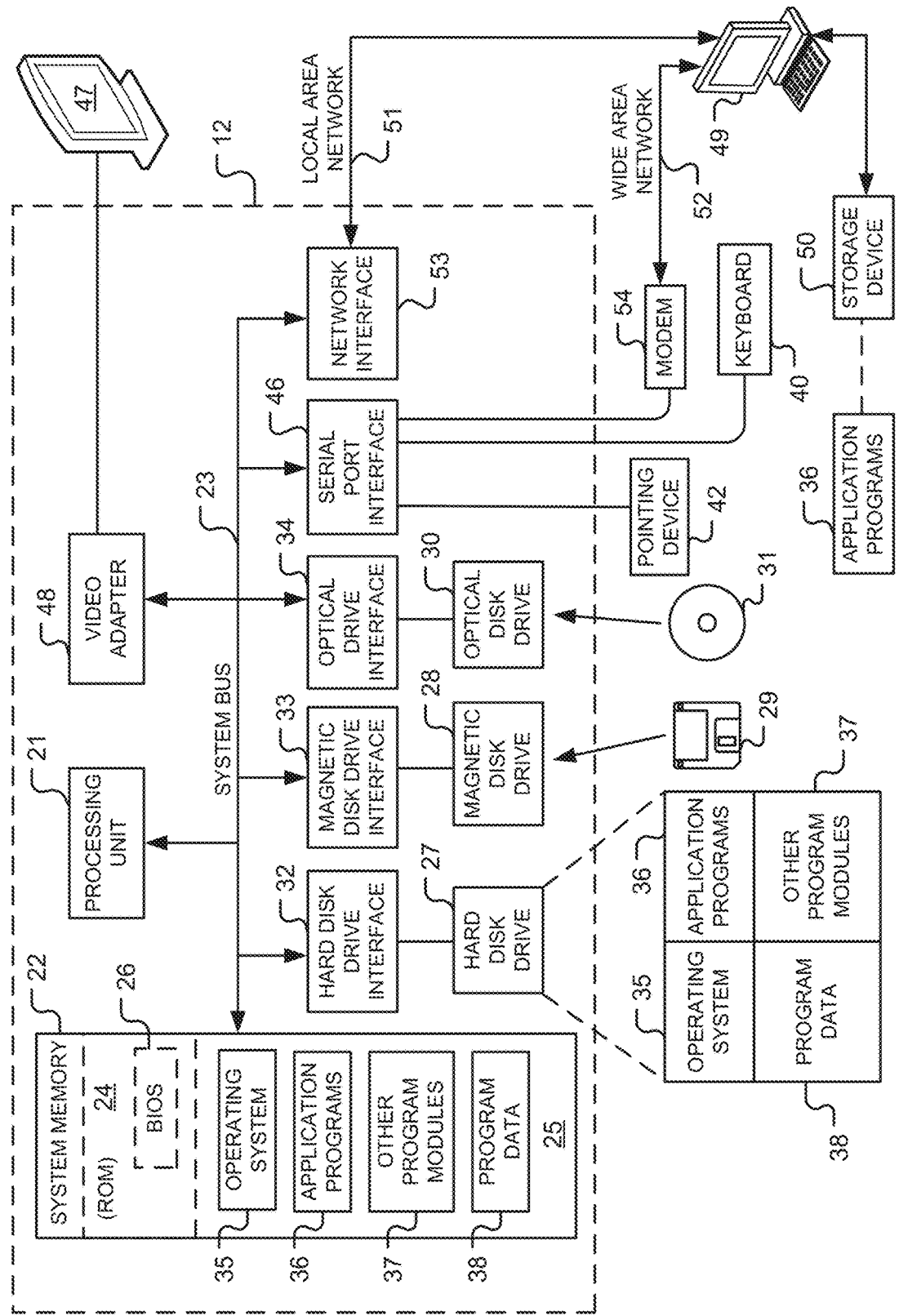
FIG. 13 shows, by way of non-limiting examples of the present invention, a block diagram of hardware and an operating environment in conjunction with which implementations of the computing devices 112, 116, 118, 124, 130, 132, and 140 (see FIG. 1) of the system 100 (see FIG. 1) may be practiced.
Figure 14:
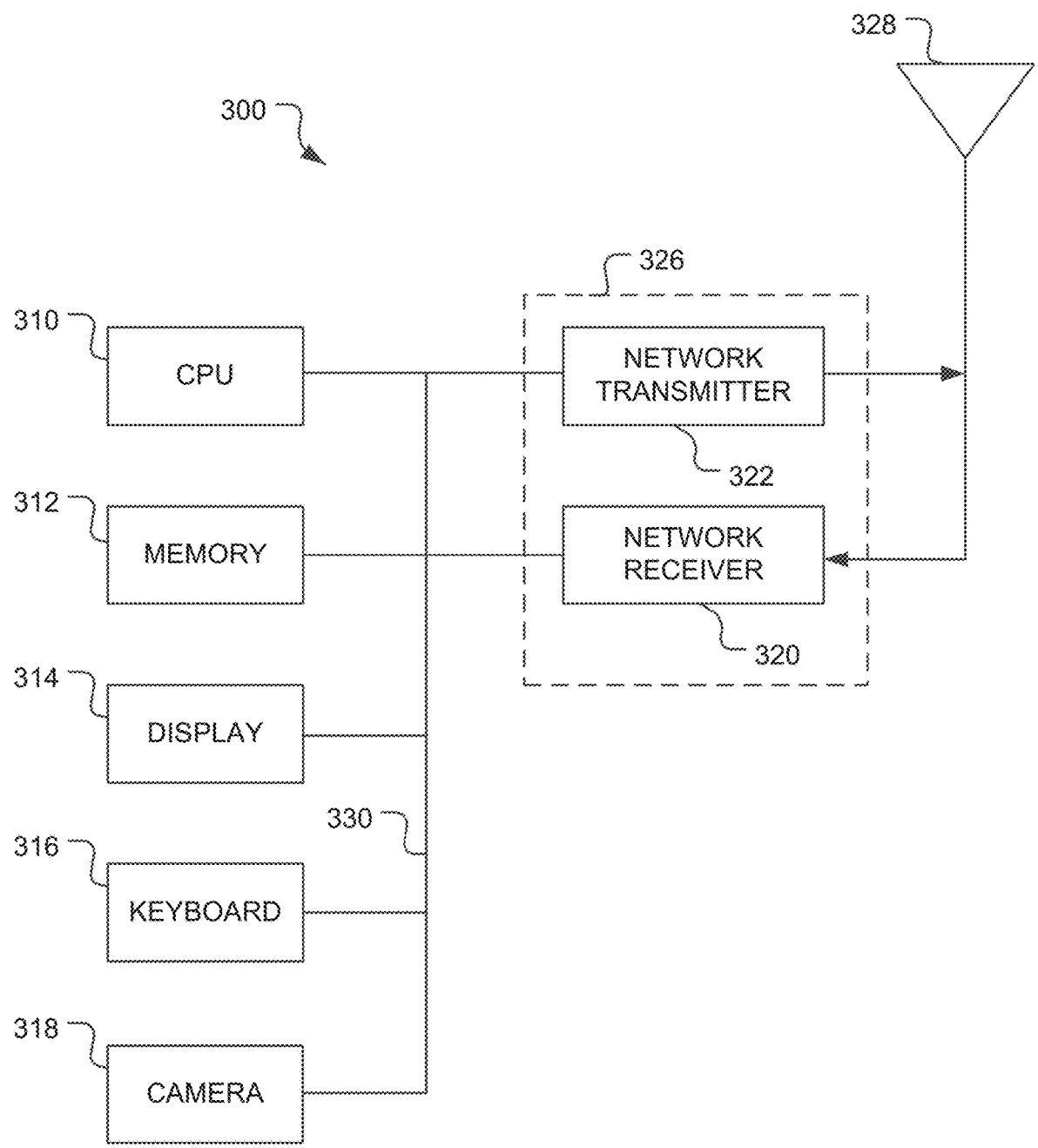
FIG. 14 shows, by way of non-limiting examples of the present invention, an exemplary mobile communication device 300.

Each of the computing devices 112, 116, 118, 124, 130, 132, and 140 may be implemented as a computing device 12 (see FIG. 13) or a mobile communication device 300 (see FIG. 14).

The mission application(s) 142 may bring all of the players to the table at once and tie large networks together. For example, the mission application(s) 142 may be configured to communicate with computing devices implementing different healthcare platforms. For example, at least some of each of the computing devices 112, 116, 118, 124, 130, and 132 may be implementing a different healthcare platform. The mission application(s) 142 may be used to interlink any number of senders (each like the sender 108) with any number of receivers (each like the receiver 110). For example, the mission application(s) 142 may be used to link rural hospitals (as sending locations) to larger urban hospitals (as receiving locations).

The mission application(s) 142 is/are configured to provide both clinical triage and transport logistics and may use care metrics to inform how the patient 102 is transported during a mission. The mission application(s) 142 may quickly and accurately triage the patient 102 and transmit relevant information to all of the different healthcare platforms. This relevant information may be received and viewed by those parties involved in the transfer of the patient 102. Thus, the mission application(s) 142 may be more efficient and provide a higher level of care than prior art methods of transferring patients. Concurrently, each part of the system 100 may be optimized for the specific patient 102 and for that patient's specific need(s). The system 100 enables the sender 108, the receiver 110, and the dispatcher 120 to predetermine care for large groups of patients and segment large groups of patients into categories based on their levels of acuity (e.g., as indicated by an acuity score 226 illustrated in FIG. 7).

The mission application(s) 142 may implement two-way communication between the sending and receiving locations 104 and 106. The mission application(s) 142 may implement two-way communication between the transport center 122 and the sending location 104. The mission application(s) 142 may implement two-way communication between the transport center 122 and the receiving location 106.

The mission application(s) 142 may be configured to perform queries of mission data (e.g., for insurance coverage issues). The mission application(s) 142 may be configured to collect and store information for future analysis and research.

The mission application(s) 142 may generate one or more dashboards (e.g., a main or dispatcher dashboard 146 illustrated in FIGS. 11A and 11B) and cause one or more of the computing devices 112, 116, 118, 124, 130, 132, and 140 to display the dashboards. The dashboards may be used to display information user input) to multiple users at remote physical locations. The dashboards may be configured to allow each sending and receiving location to see only the information pertinent to that location.

The mission application(s) 142 may generate a unique number for each transport request, mission, and/or patient that is used by the mission control computing device(s) 140 to track the mission. Thus, the mission application(s) 142 may not receive and/or store any patient identifiers.

Figure 2A:
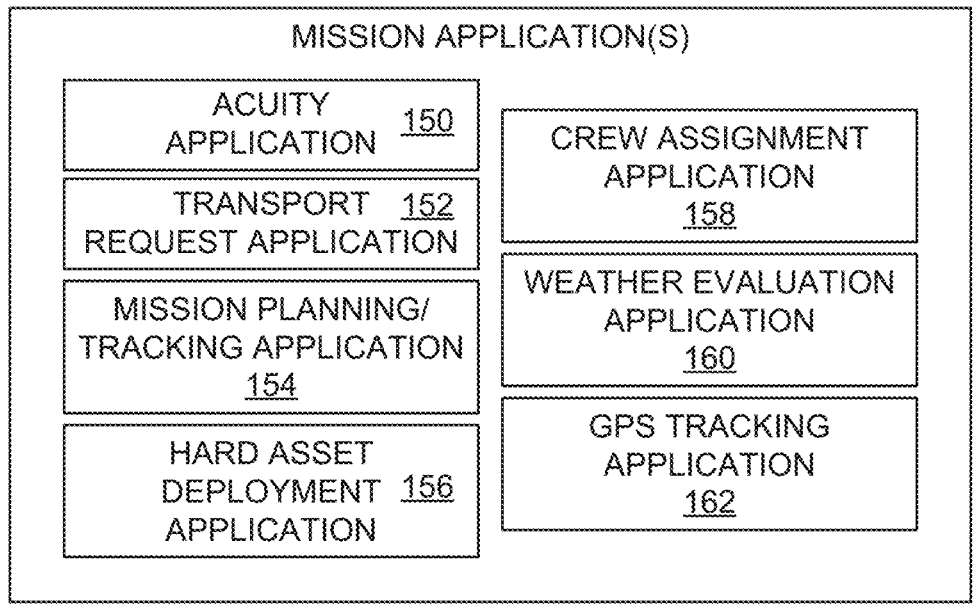
FIG. 2A shows a block diagram illustrating, by way of non-limiting examples of the present invention, exemplary mission application(s) 142.

FIG. 2A is block diagram illustrating the mission application(s) 142. In the embodiment illustrated, the mission application(s) 142 include an acuity application 150, a transport request application 152, a mission planning/tracking application 154, a hard asset deployment application 156, a crew assignment application 158, a weather evaluation application 160, and a global positioning system ("GPS") tracking application 162.

Figure 2B:
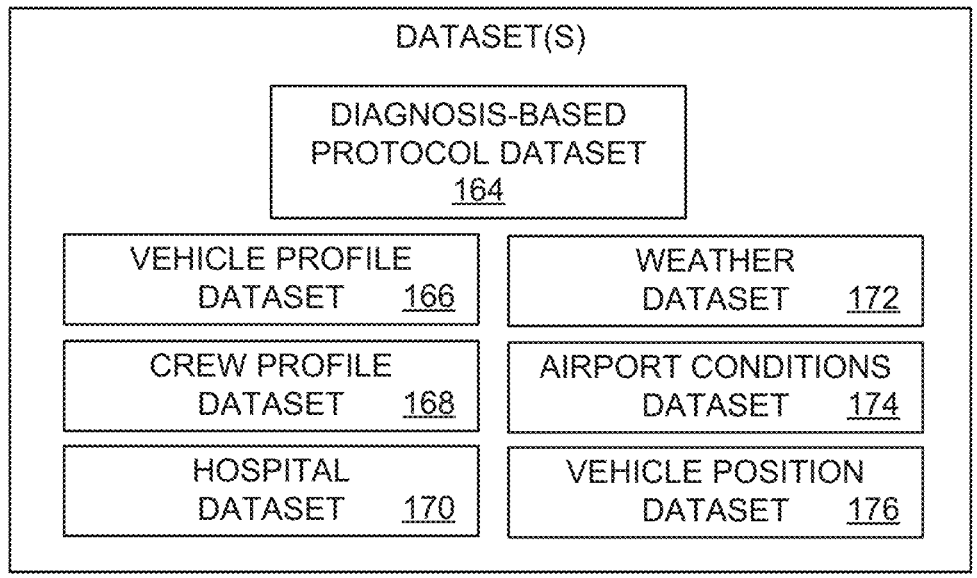
FIG. 2B shows, by way of non-limiting examples of the present invention, a block diagram illustrating exemplary dataset(s) 144.

FIG. 2B is block diagram illustrating the dataset(s) 144. In the embodiment illustrated, the dataset(s) 144 may include a diagnosis-based protocol dataset 164, a vehicle profile dataset 166, a crew profile dataset 168, a hospital dataset 170, a weather dataset 172, an airport conditions dataset 174, and/or a vehicle (e.g., aircraft) position dataset 176. The diagnosis-based protocol dataset 164 may include any predetermined protocols (e.g., for treating different medical conditions). For example, the diagnosis-based protocol dataset 164 may specify certain treatments for a stroke and different treatments for different types of strokes. The vehicle profile dataset 166 includes information for each vehicle (e.g., the vehicle 109 illustrated in FIG. 1), such as ground speed, fuel consumption, and weight limits. The crew profile dataset 168 includes information for each of the crew members 126, such as weight and experience. The hospital dataset 170 stores information about each hospital that may function as either the sending location 104 (see FIG. 1) or the receiving location 106 (see FIG. 1). The weather dataset 172 stored information about the current weather. The airport conditions dataset 174 stores the condition of one or more airports that may be used to complete a mission. The vehicle position dataset 176 stores positions of those vehicles currently conducting missions. The dataset(s) 144 may be implemented as static or dynamic datasets. For example, the crew profile dataset 168, the vehicle profile dataset 166, the hospital dataset 170, and the like may each be implemented as a static dataset. By way of another example, the weather dataset 172, the airport conditions dataset 174, the vehicle position dataset 176, and the like may each be implemented as a dynamic dataset.

Method

Figure 3:
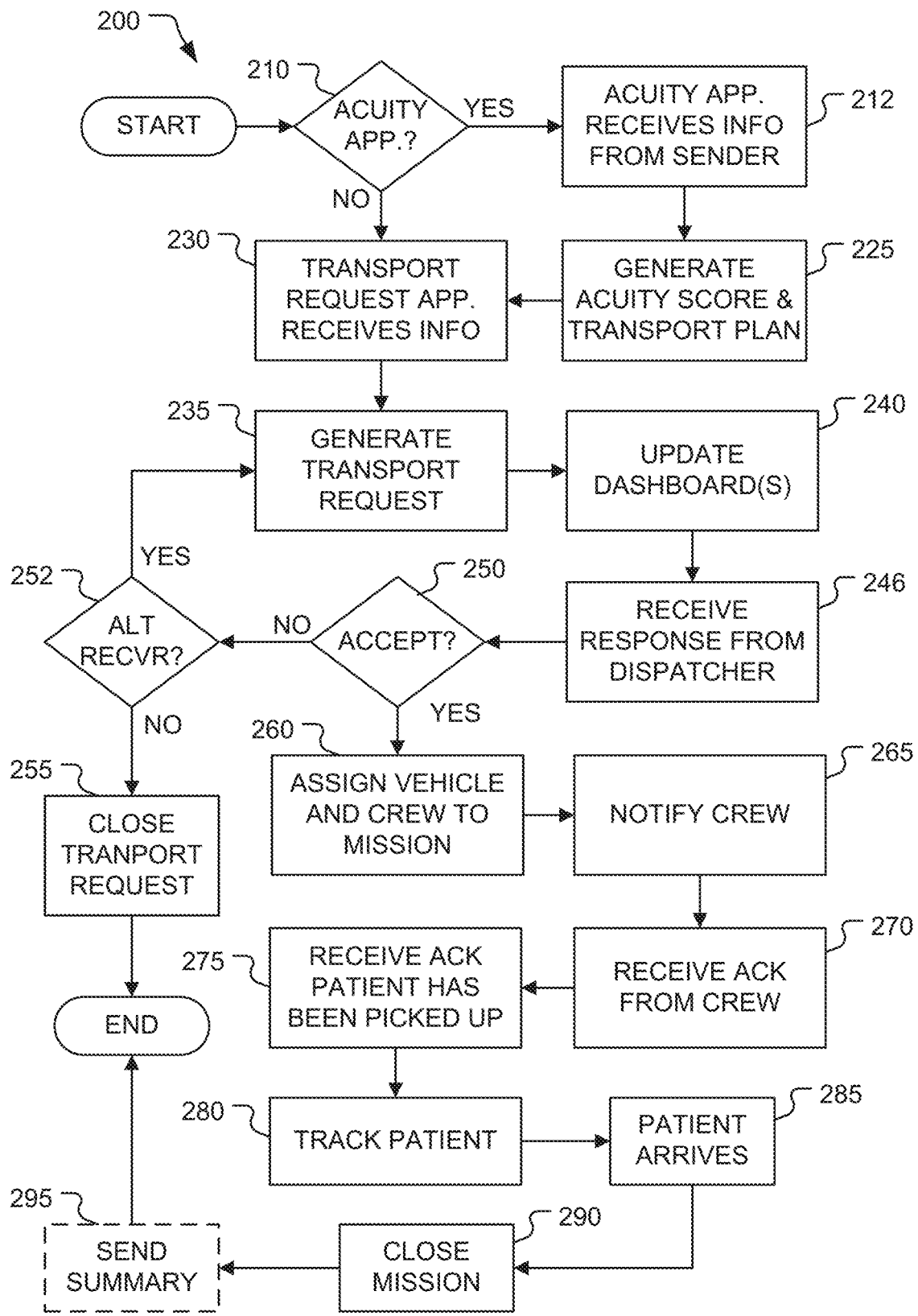
FIG. 3 shows, by way of non-limiting examples of the present invention, a flow diagram of a method 200 performed by the system 100 of FIG. 1.

FIG. 3 is flow diagram of a method 200 performed by the system 100 (see FIG. 1). The method 200 implements a mission that includes transporting the patient 102 from the sending location 104 to the receiving location 106. Referring to FIG. 2A, either the acuity application 150 or the transport request application 152 may be used by the sender 108 to initiate the mission.

Referring to FIG. 1, in first decision block 210 (see FIG. 3), the sender 108 decides whether to use the acuity application 150 (see FIG. 2A) to initiate the mission. The decision in decision block 210 is "YES," when the sender 108 decides to use the acuity application 150. By way of a non-limiting example, the acuity application 150 may be used to initiate the mission when the sender 108 is not the dispatcher 120. For example, the patient 102 may be having a heart attack and presents to the sending location 104. (e.g., an emergency room at a hospital). A doctor at the sending location 104 may decide the sending location 104 does not have the resources to care for the patient 102. Therefore, the doctor would like to transfer the patient 102 to the receiving location 106 (e.g., a different hospital). Using the sender computing device 112 (e.g., at an emergency room nurses station), the sender 108 may access the acuity application 150. For example, the sender 108 may click an icon that links to the acuity application 150, which in this example is implemented by the mission control computing device 140 as a web-based application. The web-based application displays an interface (e.g., user input screens 214, 216, 218, and 222 illustrated in FIGS. 4-9) in a web browser executing on the sender computing device 112.

In block 212 (see FIG. 3), the acuity application 150 (see FIG. 2A) receives information about the patient 102 ("patient information") and information relevant to transporting the patient 102 ("transportation information") from the sender 108. FIGS. 4-9 illustrate the exemplary user input screens 214, 216, 218, and 222 that may be generated by the acuity application 150 and di splayed to the sender 108 by the sender computing device 112. The sender 108 may use the user input screens 214, 216, and 218 to input the patient information, and the user input screen 222 to input the transportation information. The patient and/or transportation information may identify the sending location 104 (see FIG. 1) and/or the receiving location 106 (see FIG. 1). The sender computing device 112 transmits the patient and transportation information across the network 114 to the mission control computing device 140.

The patient information is used to identify severity of illness, current level of care required, anticipated or potential risk of deterioration of the condition, and time sensitive nature of the illness. Referring to FIG. 4, by way of non-limiting examples, the user input screen 214 may include one or more questions related to level of care. These questions may include one or more of the following:

1. Does the patient 102 have a time critical illness? e.g., stroke, acute MI, trauma, sepsis. (in response, the sender 108 selects YES or NO)
2. What is the care the patient 102 will need? (in response, the sender 108 selects
Floor BedTelemetryICU care or emergent treatment)
3. In the previous 2 hours, have serious symptoms needed treatment such as hemodynamic instability, arrhythmia, intractable pain, or other? (in response, the sender 108 selects YES or NO)

Referring to FIG. 5, by way of non-limiting examples, the user input screen 216 may include one or more questions related to support. For example, user input screen 216 may ask "Does their blood pressure or heart rhythm require control, either by drips or pacing? Are they receiving blood products or have they just completed receiving blood products? Is respiratory support necessary through invasive or noninvasive means?" In response, the sender 108 may select YES or NO.

Figure 6:
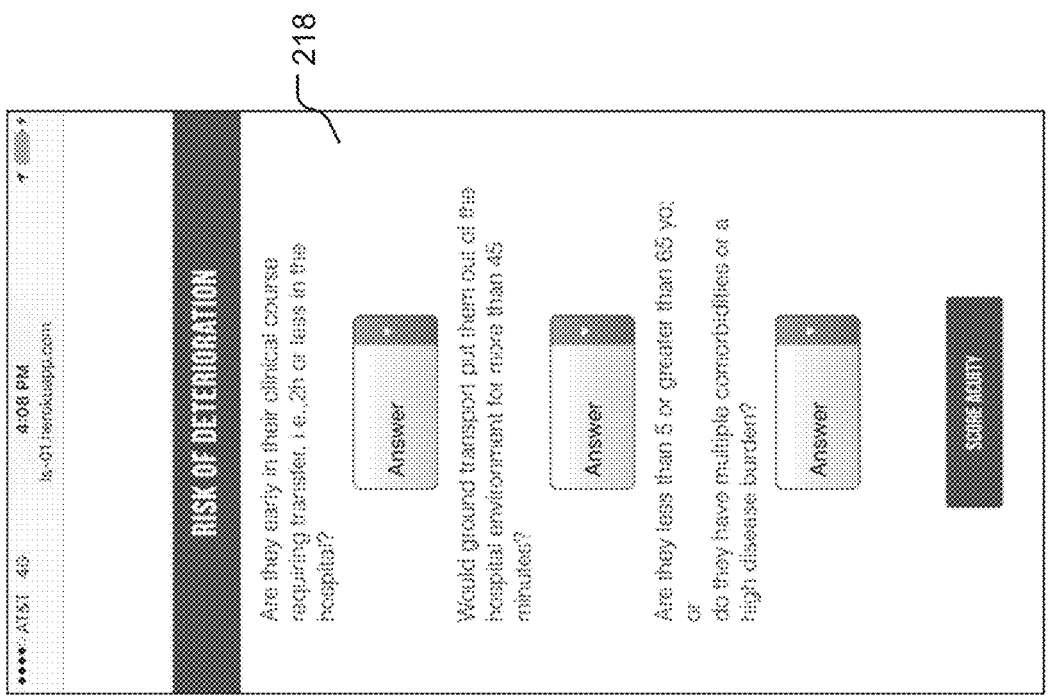
FIG. 6 shows, by way of non-limiting examples of the present invention, an exemplary user input screen 218 including one or more questions related to risk of patient deterioration.

Referring to FIG. 6, by way of non-limiting examples, the user input screen 218 may include one or more questions related to risk of deterioration. These questions may include one or more of the following:

1. Are they early in their clinical course requiring transfer, i.e., 2 hrs. or less in the hospital? (In response, the sender 108 selects YES or NO)
2. Would ground transport put them out of the hospital environment for more than 45 minutes? (In response, the sender 108 selects YES or NO)
3. Are they less than 5 or greater than 65 years old, or do they have multiple comorbidities or a high disease burden? (In response, the sender 108 selects YES or NO)

Figure 7:
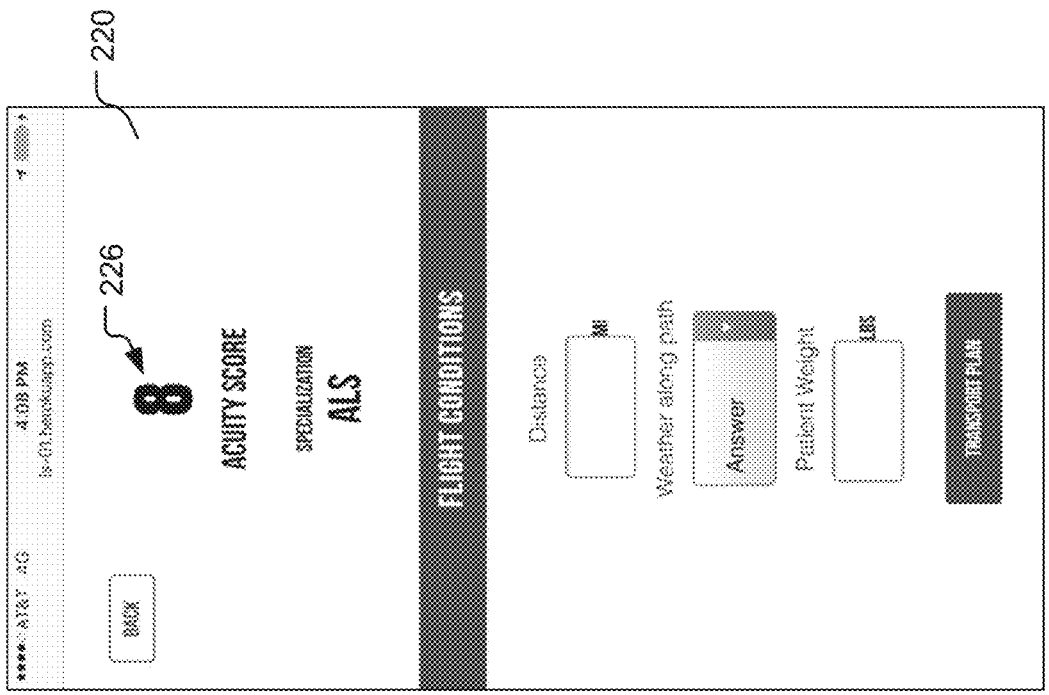
FIG. 7 shows, by way of non-limiting examples of the present invention, an exemplary user input screen 220 displaying an acuity score 226.

Information input via the user input screens 214, 216, and 218 is used by the acuity application 150 (in block 225) to generate the acuity score 226 (see FIG. 7).

Figures 8, 9:
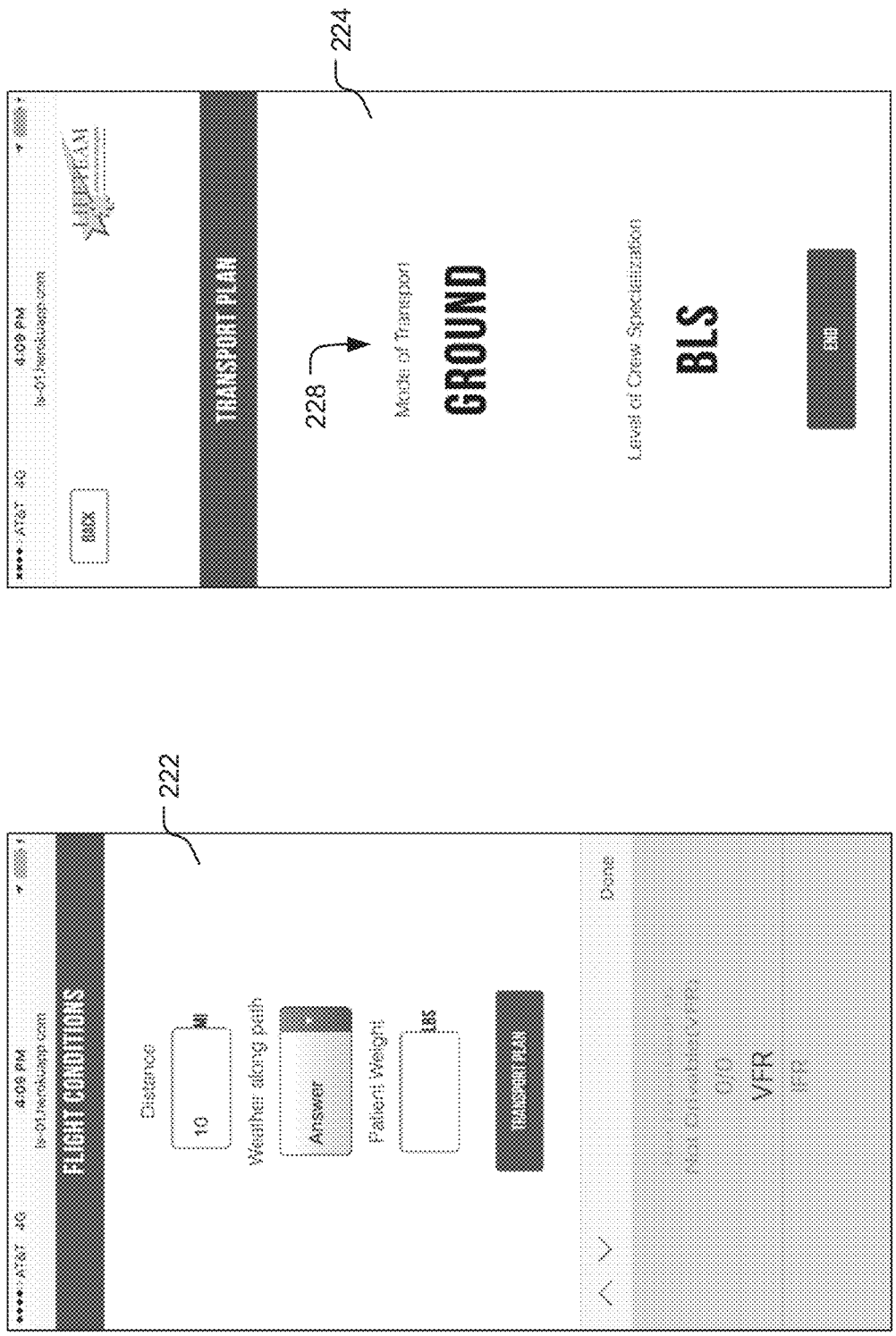
FIG. 8 shows, by way of non-limiting examples of the present invention, an exemplary user input screen 222 including one or more questions related to flight conditions.
FIG. 9 shows, by way of non-limiting examples of the present invention, an exemplary transport plan 228.

Referring to FIG. 8, by way of non-limiting examples, the user input screen 222 may include one or more questions related to flight conditions. For example, the user input screen 22.2 may ask for the patient's weight (e.g., in pounds). In response, the sender 108 may enter the weight of the patient 102. Information input via the user input screen 222 is used by the acuity application 150 (in block 225) to generate the transport plan 228 (see FIG. 9).

Together, the acuity score 226 (.see FIG. 7) and the transport plan 228 (see FIG. 9) are referred to as "mission information."

The user input screens 214, 216, 218, and 222 illustrated in FIGS. 4-9 are configured to be displayed by a web browser executing on the sender computing device 112 when the sender computing device 112 is implemented as the mobile communication device 300 (see FIG. 14). However, the user input screens 214, 216, 218, and 222 may be configured for display by other types of computing devices. For example, screens 242-245 illustrated in FIGS. 15-18 may be displayed by a web browser executing on the sender computing device 112 when the sender computing device 112 is implemented as the computing device 12 (see FIG. 13).

Figure 15:
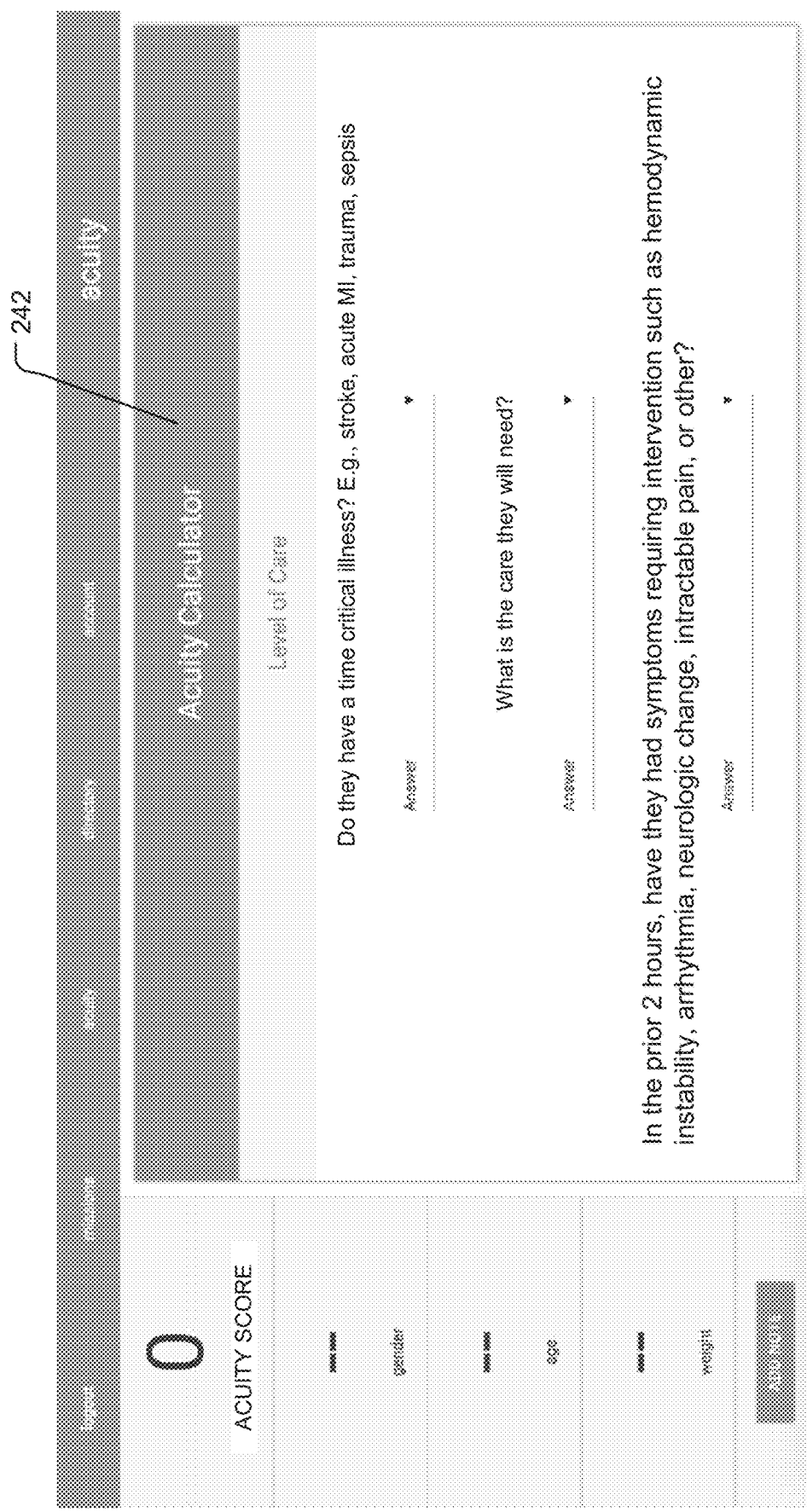
FIG. 15 shows, by way of non-limiting examples of the present invention, use of an acuity calculator screen 242 by a sender to generate an acuity score 226, as shown FIG. 16.
Figure 16:
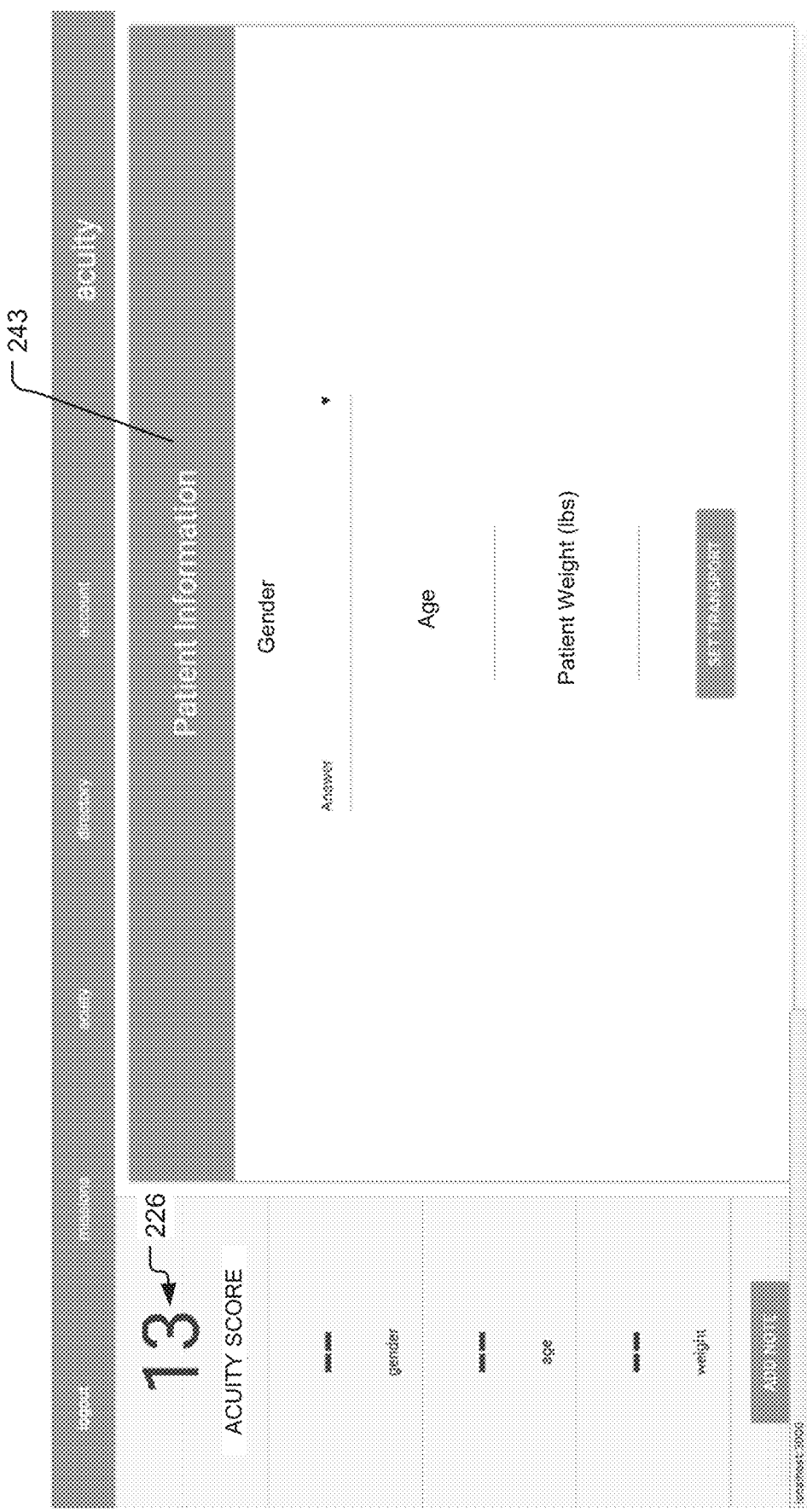
FIG. 16 shows, by way of non-limiting examples of the present invention, the acuity score 226 ("13") generated by use of the acuity calculator screen 242 of FIG. 15.

Referring to FIG. 15, the sender 108 (see FIG. 1) may use the acuity calculator screen 242 to generate the acuity score 226 (see FIG. 16). The acuity calculator screen 242 may include the same questions as the user input screens 214, 216, and 218. In the embodiment illustrated, the acuity calculator screen 242 asks the sender 108 (see FIG. 1) the following three questions and includes selectable dropdown answers for each of these questions:
  1. Do they have a time critical illness? e.g., stroke, acute MI, trauma, sepsis;
  2. What is the care they will need? and
  3. In the prior 2 hours, have they had symptoms requiring intervention such as hemodynamic instability, arrhythmia, neurologic change, intractable pain, or other?

Information input via the acuity calculator screen 242 is used by the acuity application 150 (in block 225) to generate the acuity score 226 (see FIG. 16). In the example illustrated, the acuity score 226 generated is 13.

Referring to FIG. 16, the sender 108 (see FIG. 1) may use the patient information screen 243 and the transport screen 244 (see FIG. 17) to generate the transport plan 228 (see FIG. 9). The patient information screen 243 and the transport screen 244 (see FIG. 17) may include the same questions as the user input screen 222 (see FIG. 8).

In the embodiment illustrated, the patient information screen 243 asks the sender 108 (see FIG. 1) the following three questions:
  1. Patient Gender;
  2. Patient Age; and
  3. Patient Weight (in pounds).

Figure 17:
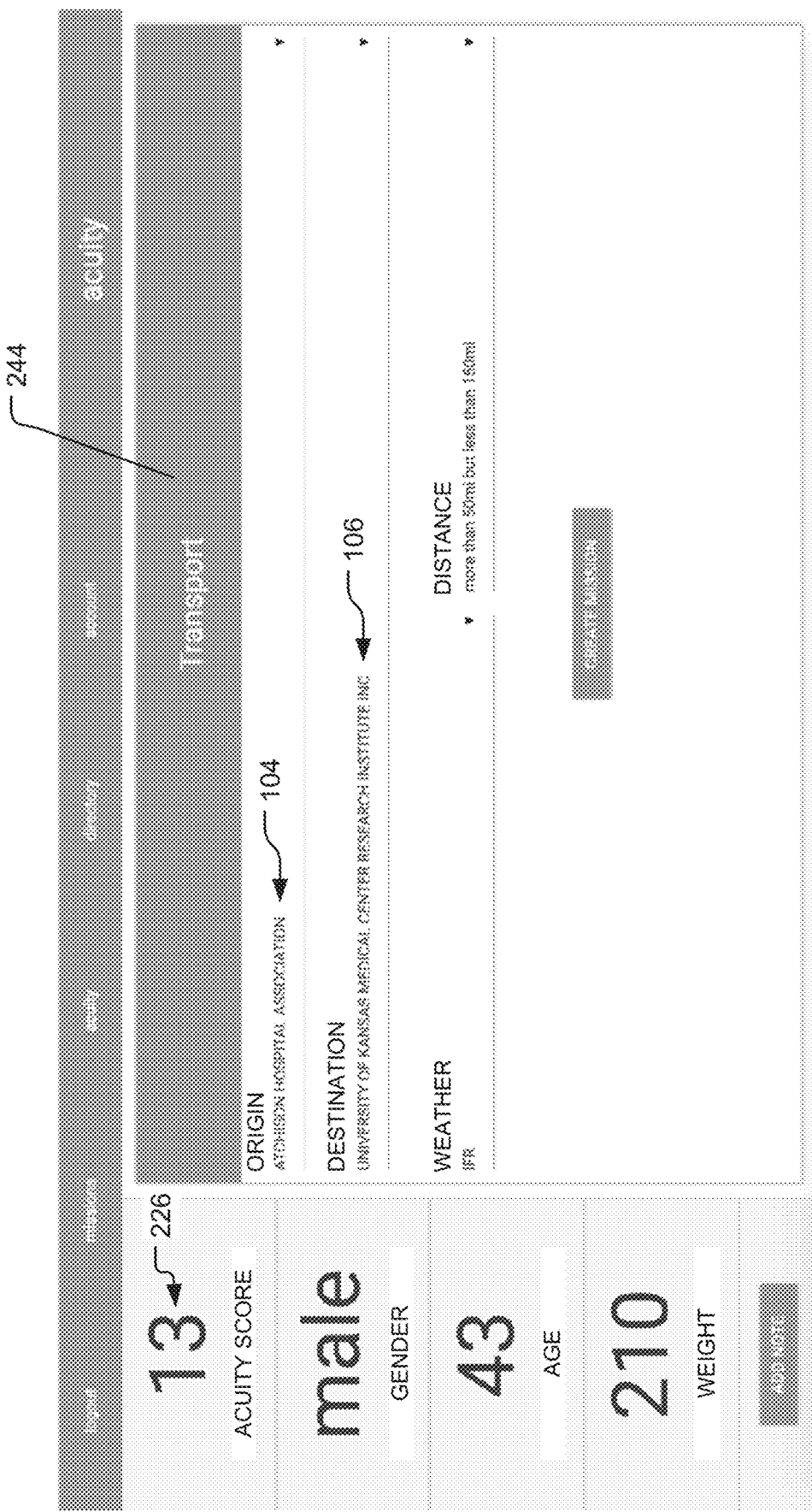
FIG. 17 shows, by way of non-limiting examples of the present invention, use of a patient information screen 243 (see FIG. 16) and of a transport screen 244 by a sender 108 to generate the transport plan 228 of FIG. 9.

Referring to FIG. 17, the transport screen 244 asks the sender 108 (see FIG. 1) to identify the sending and receiving locations 104 and 106. Optionally, the transport screen 244 may also ask the sender 108 (see FIG. 1) to input the weather and distance.

Information input via the patient information screen 243 (see FIG. 16) and the transport screen 244 (see FIG. 17) is used by the acuity application 150 (in block 225) to generate the transport plan 228 (see FIG. 9).

Figure 18:
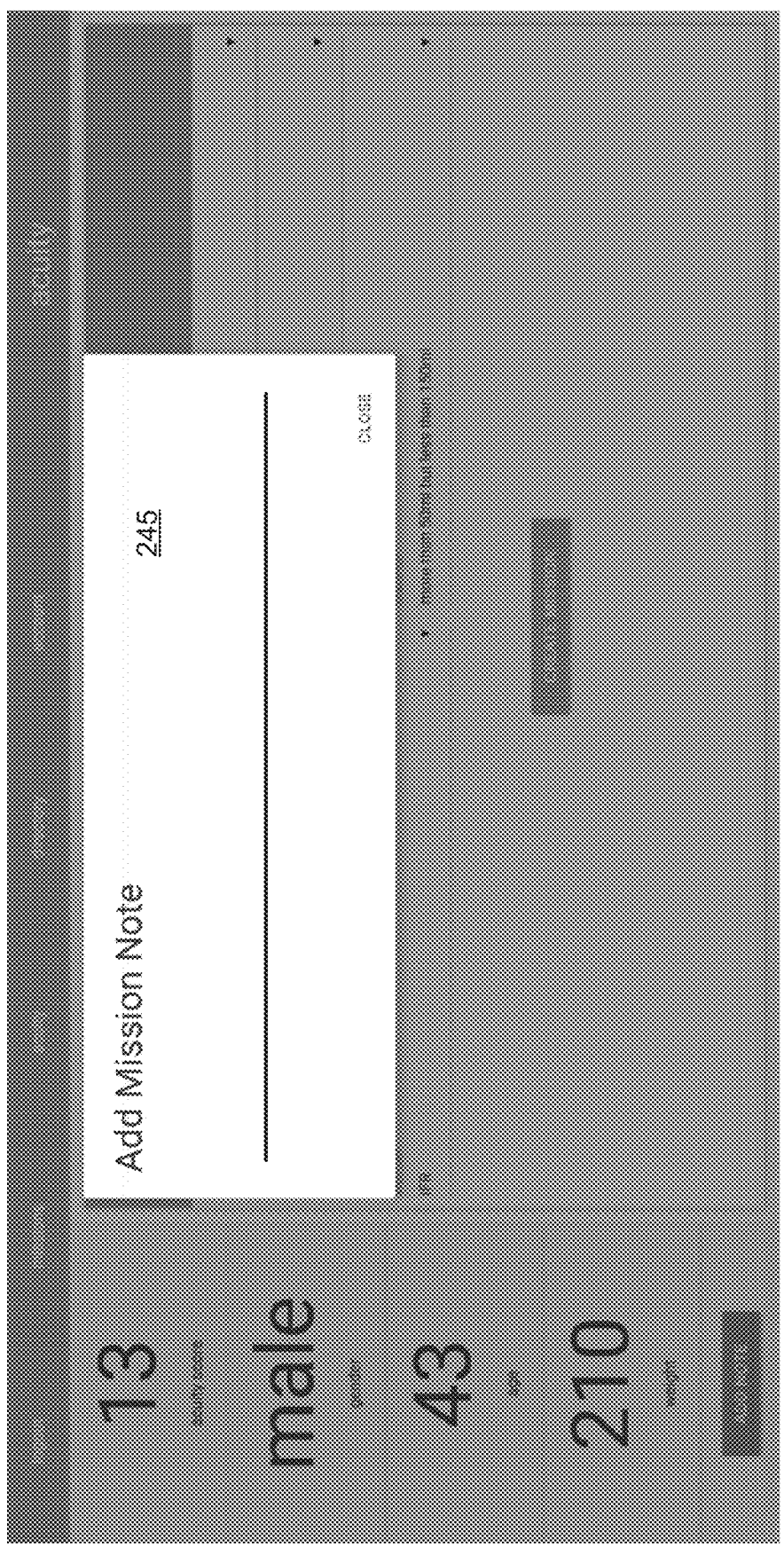
FIG. 18 shows, by way of non-limiting examples of the present invention, an optional input screen 245 that may be used by the sender 108 or the dispatcher 120 to input a note with respect to the transport request.

FIG. 18 illustrates an optional screen 245 that may be used by the sender 108 or the dispatcher 120 to input a note with respect to the transport request.

In block 225, the acuity application 150 generates an acuity score 226 (see FIGS. 7 and 16) based at least in part on the patient information and a transport plan 228 (see FIG. 9) based at least in part on the transportation information. Referring to FIGS. 2A and 2B, the acuity application 150 may access the diagnosis-based protocol dataset 164 and use its information to generate the acuity score 226 (see FIG. 7) and/or the transport plan 228 (see FIG. 9). In the embodiment illustrated, the acuity score 226 (see FIG. 7) has been implemented as integer value between one and twenty. However, this is not a requirement. For example, the acuity score 226 could be implemented differently (e.g., as a real number) and/or a different range could be used. Referring to FIG. 1, the transport plan 228 (see FIG. 9) identifies the sending location 104, the receiving location 106, a mode of transportation (e.g., air, ground, and the like) and a level of crew specialization (e.g., basic life support ("BLS"), advanced life support ("ALS"), Critical Care, and the like).

As mentioned above, the acuity application 1.50 may access the diagnosis-based protocol dataset 164 and use its information to generate the transport plan 228 (see FIG. 9). Thus, the mode of transportation and the level of crew specialization may be selected based at least in part on the severity of the patient's illness and other indicators. In other words, the acuity application 150 may rate the patient's illness acuity and match that acuity with a mode of transportation and a level of crew specialization (independently, or in unison) that is appropriate to the severity of illness. The acuity application 150 may be used to match the patient's condition with an appropriate receiving location. The acuity application 150 may consider information stored in the dataset(s) 144 (see FIG. 2B) when automatically or manually assigning the receiving location 106. For example, the acuity application 150 may take into account the weather (e.g., using information stored in the weather dataset 172 illustrated in FIG. 2B) and/or crew physical characteristics (e.g., using information stored in the crew profile dataset 168 illustrated in FIG. 2B). The acuity application 150 may also consider fuel, travel distance, travel time, physical characteristics of the patient 102, system issues (vehicles or crew availability) when automatically or manually assigning the receiving location 106.

Optionally, the acuity application 150 (see FIG. 2A) transmits the acuity score 226 (see FIG. 7) and/or the transport plan 228 (see FIG. 9) to the sender computing device 112 for display thereby to the sender 108. For example, referring to FIG. 7, the acuity score 226 may be displayed by a screen 220. By way of another non-limiting example, referring to FIG. 9, the transport plan 228 may be displayed by a screen 224. The screens 220 and 224 illustrated in FIGS. 7 and 9, respectively, are configured to be displayed by a web browser executing on the sender computing device 112 when the sender computing device 112 is implemented as the mobile communication device 300 (see FIG. 14). However, the screens 220 and 224 may be configured for display by other types of computing devices.

Referring to FIG. 2A, in next block 230 (see FIG. 3), the transport request application 152 receives the acuity score 226 (see FIG. 7) and the transport plan 228 (see FIG. 9) from the acuity application 150.

The decision in decision block 210 (see FIG. 3) is "NO," when the sender 108 decides not to use the acuity application 150 (see FIG. 2A). As mentioned above, the dispatcher 120 may function as the sender 108. By way of a non-limiting example, referring to FIG. 2A, the dispatcher 12.0 (see FIG. 1) may use the transport request application 152 (instead of the acuity application 150) to initiate the mission. When the decision in decision block 210 (see FIG. 3) is "NO," in block 230 (see FIG. 3), the transport request application 152 may receive the mission information (e.g., the acuity score 226 and/or the transport plan 228) from the dispatcher 120 (see FIG. 1). Optionally, the dispatcher 120 (see FIG. 1) may omit the acuity score 226 (see FIG. 7) from the mission information.

Figure 10:
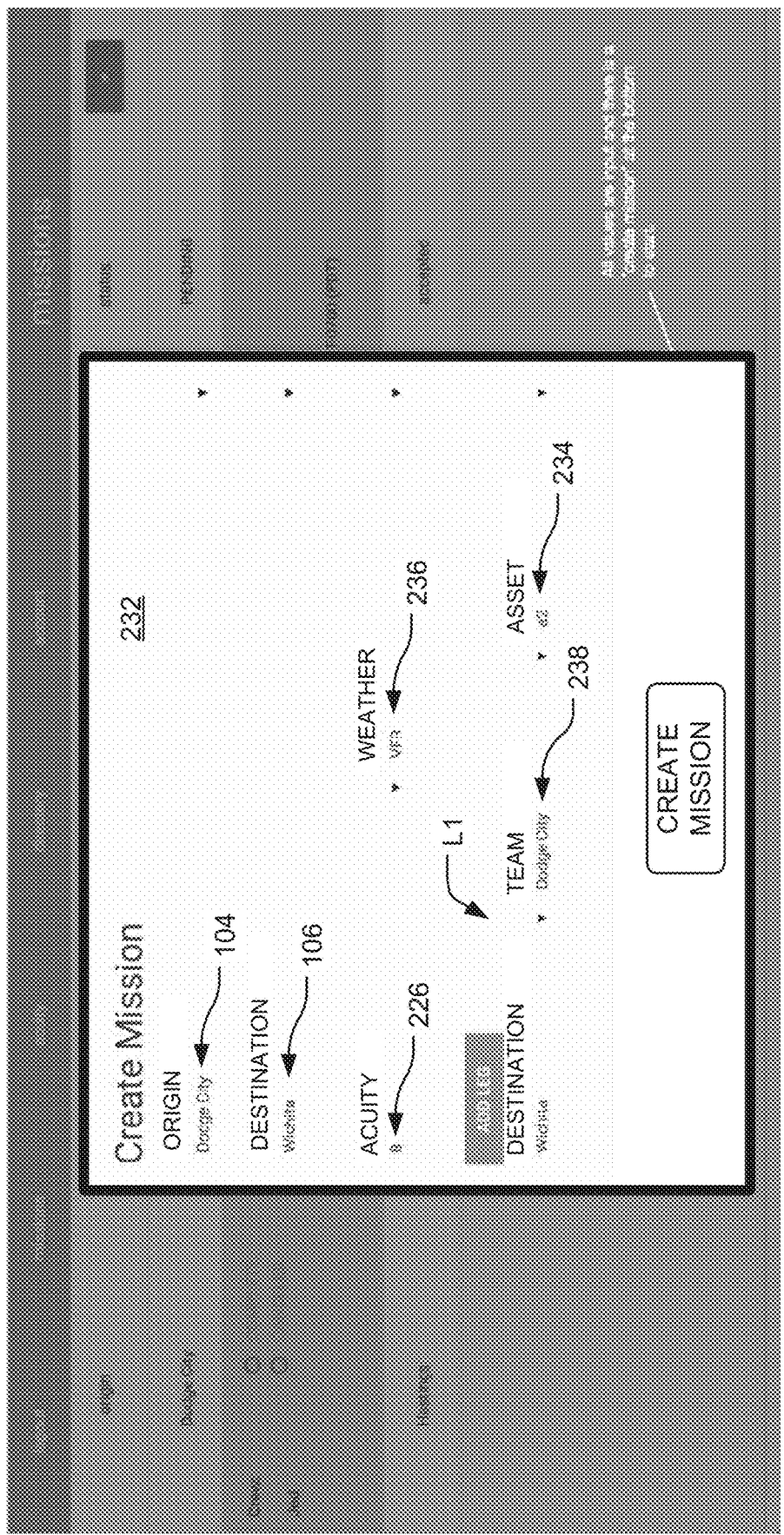
FIG. 10 shows, by way of non-limiting examples of the present invention, an exemplary mission input modal card or screen 232 that may be generated by the transport request application 152 of FIG. 2A.

By way of another example, FIG. 10 illustrates an exemplary mission input modal card or screen 232 that may be generated by the transport request application 152 (see FIG. 2A) and displayed to the dispatcher 120 (see FIG. 1) by the dispatch computing device 118 (see FIG. 1). Referring to FIG. 1, the dispatcher 120 may use the mission input screen 232 (see FIG. 10) to select the acuity score 226, the sending location 104 (labeled "origin" in FIG. 10), the receiving location 106 (labeled "destination" in FIG. 10), and the mode of transportation 234 (labeled "asset" in FIG. 10).

Optionally, the dispatcher 120 may input current weather 236. Alternatively, the current weather 236 may be obtained from the weather dataset 172 (see FIG. 2B). By way of non-limiting examples, the current weather 236 may include not drivable visual flight rules ("VFR"), not drivable instrument flight rules ("IFR"), ceiling at zero feet (or fog at ground level) and zero feet visibility ("0/0"), VFR, IFR, and the like.

In the example illustrated in FIG. 10, the acuity score 226 of the patient 102 (see FIG. 1) is eight and the patient 102 is to be transported from the sending location 104 (e.g., Dodge City) to the receiving location 106 (e.g., Wichita). The mission input screen 232 may allow the dispatcher 120 to divide the trip into one or more legs. In the example illustrated, the transport request includes only a single leg L1. The leg L1 transports the patient 102 from the sending location 104 to the receiving location 106 via the vehicle 109 (labeled "a2" in FIG. 10). The dispatcher 120 may also identify one or more of the crew members 126 (labeled "team") for each leg. In the example illustrated, those of the crew members 126 identified for the leg L1 include a "Dodge City" team 238.

Then, the dispatch computing device 118 may transmit the mission information across the network 114 to the mission control computing device 140.

In block 235 (see FIG. 3), the transport request application 152 (see FIG. 2A) generates a transport request that includes the mission information. The diagnosis-based protocol dataset 164 may provide information to the transport request application 152 that the transport request application 152 uses to generate the transport request. For example, if the patient 102 is experiencing a stroke, heart attack, trauma, and the like, the diagnosis-based protocol dataset 164 may provide information relevant to the mission.

In block 240 (see FIG. 3), the transport request application 152 (see FIG. 2A) updates the one or more dashboards (e.g., the dispatcher dashboard 146 illustrated in FIGS. 11A and 11B) with the transport request. For example, the system 100 may display the transport request on a mission control dashboard. The mission control dashboard may be viewable by the employee 121 at the mission control 141. By way of additional non-limiting examples, the mission control computing device 140 may display the transport request on a sender dashboard, a receiver dashboard, the dispatch dashboard 146 (see FIGS. 11A and 11B), and/or a crew dashboard. The receiver dashboard may display a status (e.g., accepted, rejected, and the like) of the transport request, time from initiation of the transport request, etc.

Referring to FIG. 11A, the dispatch dashboard 146 displays information about missions M1 and M2 involving the transport center 122. For example, the dispatch dashboard 146 may display the sending location 104 (see FIG. 1), the receiving location 106 (see FIG. 1), the acuity score 226, and a mission status (e.g., "pending," "accepted," "declined," "closed," and the like). In the embodiment illustrated, the mission M1 has the status "pending," and the mission M2 has the status "accepted." The dispatch dashboard 146 may also display a current leg (e.g., "0 of 1"), a current crew e.g., "Jed") assigned to the current leg, and a status of the current leg (e.g., complete or canceled). When the status of the current leg is "complete" and the mission has a next leg, the next leg becomes the current leg. On the other hand, if the status of the current leg is "canceled," the mission is canceled and its information stored. The dispatch dashboard 146 may include a link (e.g., labeled "+") to the mission input screen 232 (see FIG. 10).

Figure 11B:
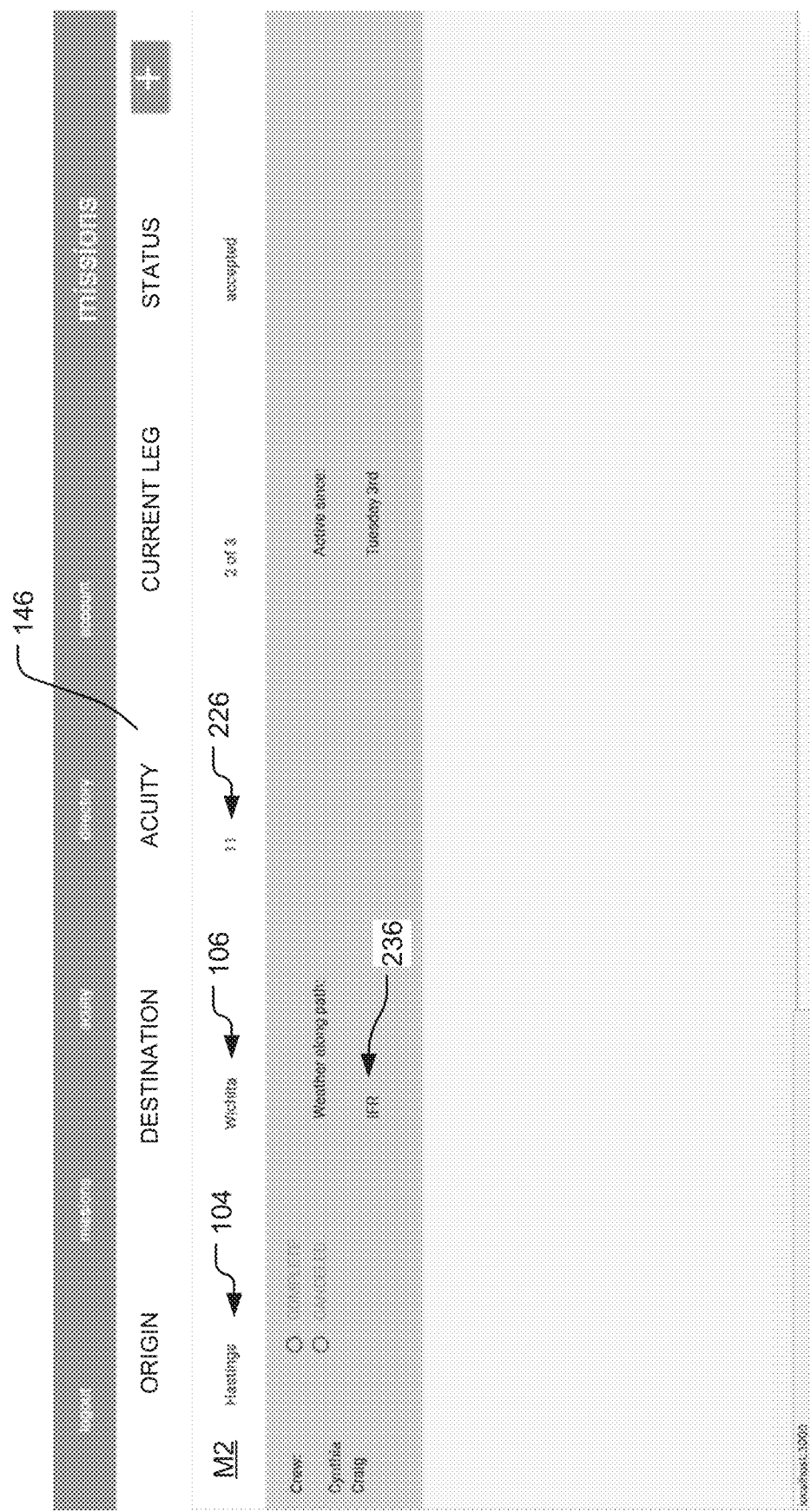
FIG. 11B shows, by way of non-limiting examples of the present invention, a dispatch dashboard 146 displaying information about the mission M2.

In FIG. 11B, the dispatch dashboard 146 displays information about the mission M2. In the example illustrated, the current leg of the mission M2 is a second leg of three legs (e.g., "2 of 3"). A current crew "Cynthia" and "Craig") is assigned to the current leg. The current weather 236 is IFR.

In decision block 246 (see FIG. 3), the transport request application 152 (see FIG. 2A) receives a response from the dispatcher 120. For example, the dispatcher 120 may call the receiver 110 and receive a verbal acceptance or rejection of the transport request. The dispatcher 120 provides this response to the transport request application 152 (see FIG. 2A). The transport request application 152 may also receive acknowledgement of the transport request from the receiver 110 and/or the dispatcher 120 before the response is received. Optionally, when the receiver 110 accepts the transport request, the receiver 110 may provide additional information, such as a room number, a receiving physician name, etc.

When the dispatcher 120 rejects the transport request, the decision in decision block 250 (see FIG. 3) is "NO," When the decision in decision block 250 (see FIG. 3) is "NO," the transport request application 152 (see FIG. 2A) advances to block 252. In decision block 252, the transport request application 152 (see FIG. 2A) determines whether the dispatcher 120 has selected an alternate receiving location (not shown). The decision in decision block 252 (see FIG. 3) is "YES" when the dispatcher 120 has selected an alternate receiving location (not shown). Otherwise, the decision in decision block 252 (see FIG. 3) is "NO."

When the decision in decision block 252 (see FIG. 3) is "YES," the transport request application 152. (see FIG. 2A) returns to block 235 and regenerates the transport request.

On the other hand, when the decision in decision block 252 (see FIG. 3) is "NO," in block 255, the transport request application 152 (see FIG. 2A) closes the transport request. Then, the method 200 terminates.

The decision in decision block 250 (see FIG. 3) is "YES" when the dispatcher 120 accepts the transport request. When this occurs, the transport request is converted into a mission by the mission planning/tracking application 154 (see FIG. 2A). Additionally, in block 260, the mission planning tracking application 154 assigns an appropriate vehicle (a rotor wing aircraft, a fixed wing aircraft, or a ground unit) to transport the patient 102. The mission planning/tracking application 154 may also assign of one or more of the crew members 126 having the level of crew specialization specified in the transport plan 228 (see FIG. 9) to accompany the patient 102.

Figure 12:
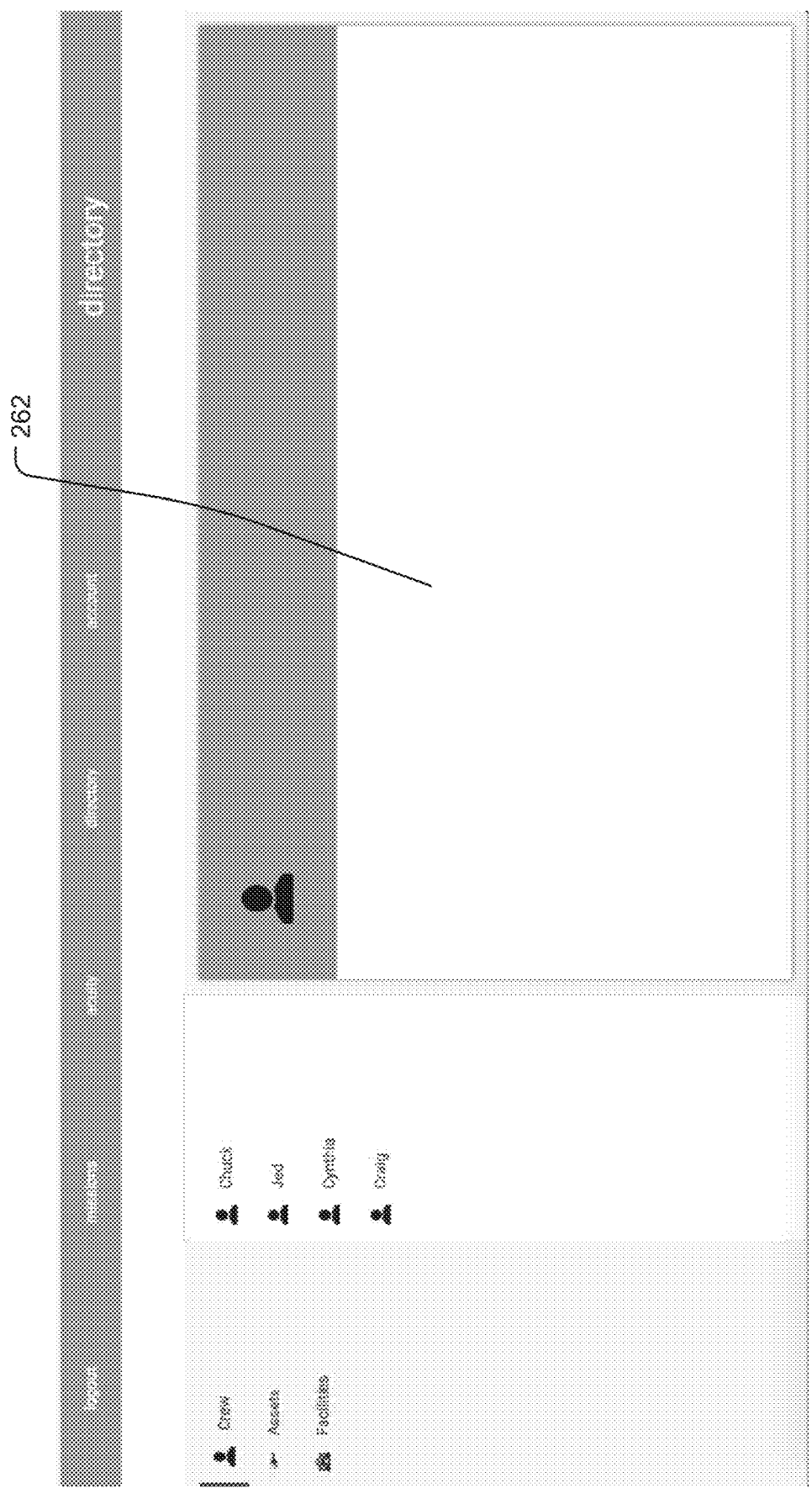
FIG. 12 shows, by way of non-limiting examples of the present invention, a user input screen 262 for assigning vehicle and crew member(s) to a mission.
Figure 19:
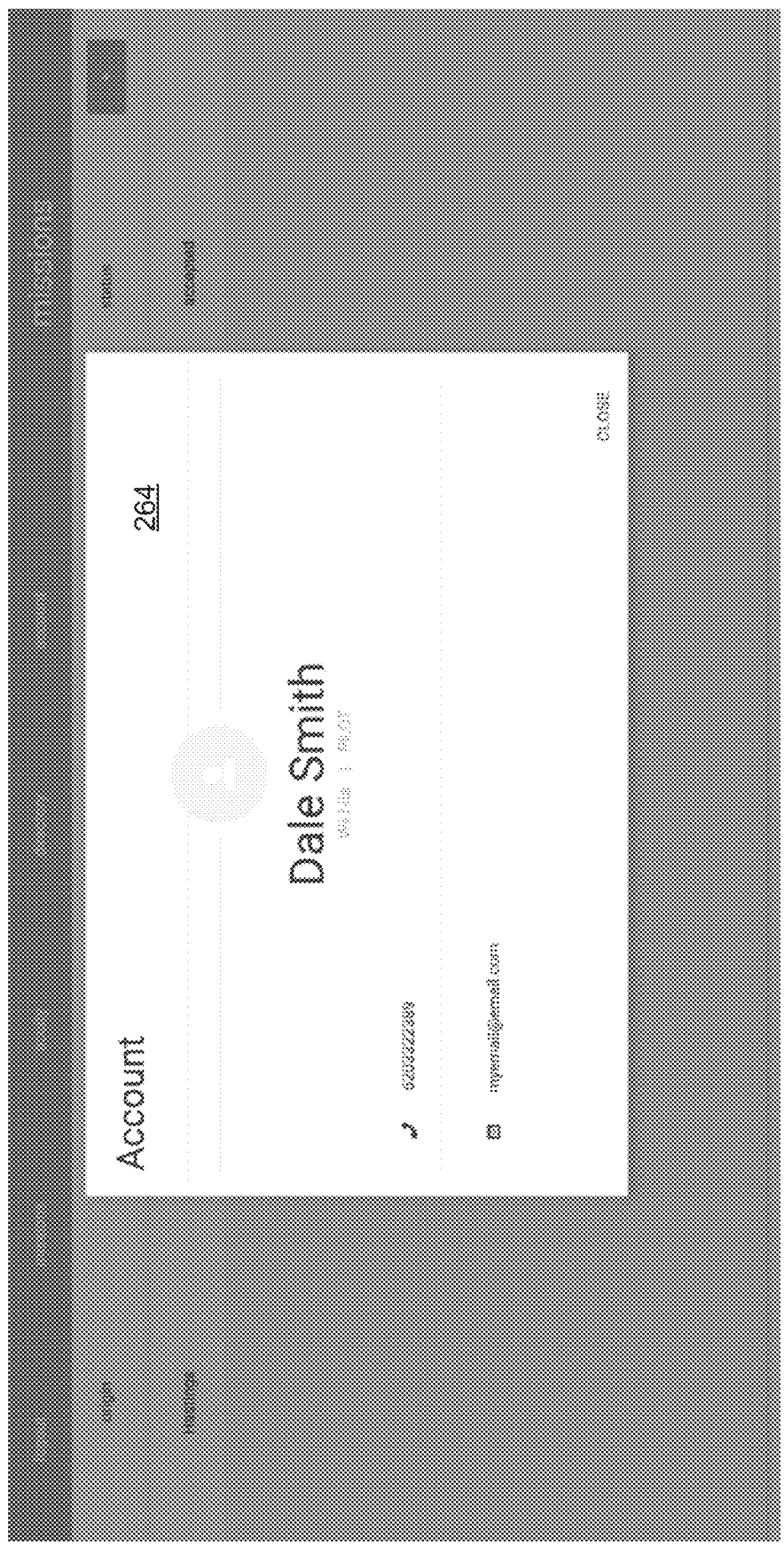
FIG. 19 shows, by way of non-limiting examples of the present invention, a member modal card 264 viewable by the dispatcher 120.

Optionally, the vehicle and crew member(s) may be selected by the dispatcher 120 for assignment by the mission planning/tracking application 154 (see FIG. 2A). For example, the dispatcher 120 may have entered this information in the mission input screen 232 (see FIG. 10). By way of another non-limiting example, the dispatcher 120 may use a user input screen 262 (see FIG. 12) to assign the vehicle and crew member(s) to the mission. By clicking on one of the crew members 126, the dispatcher 120 may view a member modal card 264 (see FIG. 19). By clicking on one of the vehicles (labeled "assets" in FIG. 12), the dispatcher 120 may view an asset page.

Alternatively, the mission planning/tracking application 154 may assign the vehicle and crew member(s) to the mission automatically. The mission planning/tracking application 154 may use the hard asset deployment application 156 to assign the vehicle 109 to the mission and the crew assignment application 158 to assign the crew member(s) to accompany the patient 102. Optionally, the hard asset deployment application 156 may use a vehicle profile dataset 166 to identify vehicles that are appropriate for the mission. Optionally, the crew assignment application 158 may use a crew profile dataset 168 to identify those of the crew members 126 who are appropriate for the mission. The mission planning/tracking application 154 may consider weather (e.g., using the weather evaluation application 160 illustrated in FIG. 2A), resource availability, proximity, efficiency, cost, and reimbursement to optimize efficiencies in the system 100. For example, while the first transport base 128 may have the crew members 126, its helicopter may be unavailable due to maintenance. This would cause the mission planning/tracking application 154 to select the next closest resource at the second transport base 134 and match that resource with the crew members 126 at the first transport base 128. By way of another non-limiting example, the mission planning/tracking application 154 might know that the first and second transport bases 128 and 134 are substantially the same distance from the sending location 104. The mission planning/tracking application 154 might also know that the history of the first transport base 128 suggests a high likelihood of a mission in its own area and the history of the second transport base 134 suggests has a much lower likelihood of a mission in its own area. Thus, in this example, the mission planning/tracking application 154 (see FIG. 2A) gives the second transport base 134 preference over the first transport base 128. Additionally, the mission planning/tracking application 154 may receive crew and vehicle profiles (e.g., from the vehicle and crew profile datasets 166 and 168 illustrated in FIG. 2B) that may be used to calculate weight, balance, and fuel requirements. For this example, if the patient 102 weighs more than 300 lbs., the patient 102 cannot be transported via a rotor wing aircraft. Additionally, the weather may require instrument only flying (or IFR). Therefore, a fixed wing aircraft may be dispatched.

By way of non-limiting examples, the mission planning/tracking application 154 may take into account the weather, crew physical characteristics, fuel, travel distance, travel time, physical characteristics of the patient 102, system issues (vehicles or crew availability) to automatically or manually assign the appropriate resources to the mission.

When the mission planning/tracking application 154 automatically assigns the vehicle and crew member(s) to the mission, the mission planning/tracking application 154 may receive a verification of these assignments from the dispatcher 120.

In block 265 (see FIG. 3), the mission planning/tracking application 154 (see FIG. 2A) notifies the crew member(s) of the assignments made in block 260 (see FIG. 3). For example, the mission planning/tracking application 154 may add the assignments to the crew dashboard.

In block 270 (see FIG. 3), the mission planning/tracking application 154 (see FIG. 2A) receives acknowledgements from the crew member(s). For example, the mission planning/tracking application 154 (see FIG. 2A) may receive acknowledgements from the crew computing device(s) 124 operated by those of the crew members 126 assigned to the mission.

In block 275 (see FIG. 3), the mission planning/tracking application 154 (see FIG. 2A) receives an indication that the patient 102 has been picked up or the aircraft has taken off. Additionally, the mission planning/tracking application 154 (see FIG. 2A) may update the dashboards 146 (see FIGS. 11A and 11B) with this information. At this point, a sufficient "handshake" has occurred between the sender 108, the receiver 110, and the dispatcher 120 to transfer command and responsibility for the patient 102 from the sending location 104 to the transport center 122.

In block 280 (see FIG. 3), the mission planning/tracking application 154 (see FIG. 2A) may track the patient 102. For example, the mission planning/tracking application 154 may access the GPS tracking application 162 (see FIG. 2A), which receives location information from the vehicle 109 transporting the patient 102 and/or one of the crew member(s) traveling with the patient 102. Thus, as the patient 102 moves, the dashboards 146 (see FIGS. 11A and 11B) may display updated location information (e.g., on a dispatch map) and an estimated time of arrival ("ETA"). Optionally, the location information may be stored in the vehicle position dataset 176 (see FIG. 2B).

In block 285 (see FIG. 3), the mission planning/tracking application 154 (see FIG. 2A) receives a notification from the dispatcher 120 that the patient 102 has been delivered to the receiving location 106. At this point, a sufficient "handshake" has occurred between the sender 108, the receiver 110, and the dispatcher 120 to transfer command and responsibility for the patient 102 from the transport center 122 to the receiving location 106.

In block 290 (see FIG. 3), the mission planning/tracking application 154 (see FIG. 2A) closes the mission. Optionally, the mission planning/tracking application 154 (see FIG. 2A) may be required to receive a close instruction from the sender 108, the receiver 110, and/or the dispatcher 12.0 before closing the mission. In optional block 295 (see FIG. 3), the mission planning/tracking application 154 may send a mission summary to the sending and receiving locations 104 and 106. Then, the method 200 terminates.

The method 200 (see FIG. 3) allows the receiver 110 and/or the dispatcher 120 to input initial transport data. Thus, the receiver 110 may input the patient and transportation information for the sending location 104, which allows the mission control computing device 140 to work with senders and sending locations that do not have access to the mission control computing device 140. Additionally, the dispatcher 120 may input the patient and transportation information for third parties, such as Highway Patrol (e.g., when the Highway Patrol calls for a helicopter to respond to an injury accident on a roadway).

The mission planning/tracking application 154 (see FIG. 2A) allows the crew members traveling with the patient 102 to enter changes to the patient's condition as the patient 102 is being transported (e.g., in block 280). This allows the receiving location 106 to make any necessary preparations before receiving the patient 102. The mission planning/tracking application 154 (see FIG. 2A) may be configured to allow cross communication between the relevant parties to the mission (e.g., the sender 108, the receiver 110, crew members traveling with the patient 102, and/or the dispatcher 120). The mission planning/tracking application 154 (see FIG. 2A) may he configured to update the patient's condition, update the patient's orders, and/or modify the transport plan based on information provided to the mission planning/tracking application 154 by any of these relevant parties.

Computing Device

FIG. 13 is a block diagram of hardware and an operating environment in conjunction with which implementations of the computing devices 112, 116, 118, 124, 130, 132, and 140 (see FIG. 1) of the system 100 (see FIG. 1) may be practiced. The description of FIG. 13 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those of ordinary skill in the art will appreciate that implementations may be practiced with other computer system configurations, including the mobile communication device 300 (see FIG. 14), hand-held devices, multiprocessor systems, microprocessor-based or programmable consumer electronics, network PCs, minicomputers, mainframe computers, and the like. Implementations may also be practiced in distributed computing environments (e.g., cloud computing platforms) where tasks are performed by remote processing devices that are linked through a communications network (e.g., the network 114). In a distributed computing environment, program modules may be located in both local and remote memory storage devices.

The exemplary hardware and operating environment of FIG. 13 includes a general-purpose computing device in the form of the computing device 12. By way of non-limiting examples, the computing device 12 may be implemented as a laptop computer, a tablet computer, a web enabled television, a personal digital assistant, a game console, a smartphone, a mobile computing device, a cellular telephone, a desktop personal computer, a blade computer, and the like.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like.

The computing device 12 ay be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those of ordinary skill in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including the operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types of physical feedback (e.g., a force feedback game controller).

The input devices described above are operable to receive user input and selections. Together the input and display devices may be described as providing a user interface. The user interface is configured to display the various screens (e.g., the screens 214-224, 232, 242-245, 262, and 264) and dashboards (e.g., the dashboard 146) described above and receive input entered into any of these screens.

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device. The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 13 include a local-area network (LAN) 51 and a wide-area network (WAN) 52. Such networking environments are commonplace in offices, enterprise-wide computer networks, intranets and the Internet. The network 114 (see FIG. 1) may be implemented using one or more of the LAN 51 or the WAN 52 (e.g., the Internet).

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the LAN 51 through a network interface or adapter 53, which is one type of communications device. When used in a WAN-networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

In some embodiments, the system memory 22 stores computer executable instructions (e.g., all or portions of the mission application(s)142 illustrated in FIGS. 1 and 2A) that when executed by one or more processors cause the one or more processors to perform all or portions of the method 200 illustrated in FIG. 3 and described above. The system memory 22 may also store the dataset(s) 144 (see FIGS. 1 and 2B). Such instructions and/or dataset(s) 144 may be stored on one or more non-transitory computer-readable or processor readable media.

Mobile Communication Device

FIG. 14 is a functional block diagram illustrating the mobile communication device 300 that may be used to implement one or more of the computing devices 112, 116, 118, 124, 130, 132, and 140 (see FIG. 1) of the system 100 (see FIG. 1). The mobile communication device 300 may be implemented as a cellular telephone, smart phone, a tablet computing device, and the like. By way of a non-limiting example, the mobile communication device 300 may be implemented as a smartphone executing IOS or Android OS.

The mobile communication device 300 includes a central processing unit ("CPU") 310. Those skilled in the art will appreciate that the CPU 310 may be implemented as a conventional microprocessor, application specific integrated circuit (ASIC), digital signal processor (DSP), programmable gate array (PGA), or the like. The mobile communication device 300 is not limited by the specific form of the CPU 310.

The mobile communication device 300 also contains the memory 312. The memory 312 may store instructions and data to control operation of the CPU 310. The memory 312 may include random access memory, ready-only memory, programmable memory, flash memory, and the like. The mobile communication device 300 is not limited by any specific form of hardware used to implement the memory 312. The memory 312 may also be integrally formed in whole or in part with the CPU 310.

The mobile communication device 300 also includes conventional components, such as a display 314, a keypad or keyboard 316, and a camera or video capture device 318. For example, the display 314 may be implemented as conventional touch screen display. These are conventional components that operate in a known manner and need not be described in greater detail. Other conventional components found in wireless communication devices, such as USB interface, Bluetooth interface, infrared device, and the like, may also be included in the mobile communication device 300. For the sake of clarity, these conventional elements are not illustrated in the functional block diagram of FIG. 14.

The display 314, the keyboard 316, and the camera or video capture device 318 are operable to receive user input and selections. Together the input and display devices may be described as providing a user interface. The user interface is configured to display the various screens (e.g., the screens 214-224, 232, 242-245, 262, and 264) and dashboards (e.g., the dashboard 146) described above and receive input entered into any of these screens.

The mobile communication device 300 also includes a network transmitter 322 such as may be used by the mobile communication device 300 for normal network wireless communication with a base station (not shown). FIG. 14 also illustrates a network receiver 320 that operates in conjunction with the network transmitter 322 to communicate with the base station (not shown). In a typical embodiment, the network transmitter 322 and network receiver 320 are implemented as a network transceiver 326. The network transceiver 326 is connected to an antenna 328. Operation of the network transceiver 326 and the antenna 328 for communication with a wireless network (not shown) is well-known in the art and need not be described in greater detail herein.

The mobile communication device 300 may also include a conventional geolocation module (not shown) operable to determine the current location of the mobile communication device 300.

The various components illustrated in FIG. 14 are coupled together by the bus system 330. The bus system 330 may include an address bus, data bus, power bus, control bus, and the like. For the sake of convenience, the various busses in FIG. 14 are illustrated as the bus system 330.

The memory 312 may store instructions (e.g., all or portions of the mission application(s) 142 illustrated in FIGS. 1 and 2A) executable by the CPU 310. When executed by the CPU 310, the instructions may cause the CPU 310 to perform to perform all or portions of the method 200 illustrated in FIG. 3 and described above. The memory 312 (see FIG. 14) may also store the dataset(s) 144 (see FIGS. 1 and 2B). Such instructions and/or dataset(s) 144 may be stored on one or more non-transitory computer or processor readable media.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

What is claimed is:

1. A triaged patient transport method for use with a mission control computing device configured to execute and implement one or more application modules, and in operative communication over a network with a sender computing device, a dispatch computing device, and a receiver computing device, each operable to display one or more dashboards and/or input screens, and with one or more static or dynamic mission control datasets, the method comprising:

receiving, by an acuity module (AM), inputted patient and transportation information from the sender computing device, and generating by the AM a patient acuity score and a patient transport plan, wherein the transport plan comprises a sending location, an appropriate receiving location, a mode of transportation, and a level of crew specialization, and wherein the acuity score is matched, independently or in unison, with the transportation mode, the crew specialization level, and the appropriate receiving location;

receiving, by a transport request module (TRM), the acuity score and the transport plan, generating by the TRM a transport request that includes the acuity score and the transport plan, updating by the TRM one or more dashboards, including a dispatcher dashboard on the dispatch computing device at a transport center, with the transport request, and receiving, by the TRM, a receiver (receiving location) acceptance response for the transport request from the dispatch computing device;

converting, by a mission planning and tracking module (MPTM), the accepted transport request into a transport mission that assigns an appropriate vehicle to transport the patient, and that optionally assigns one or more crew members having the level of crew specialization specified in the transport plan, receiving by the MPTM a crew acknowledgement, receiving, by the MPTM, real-time indication that the patient has been picked up for transport, and updating by the MPTM one or more dashboards, including the dispatcher dashboard, to provide a coordinated handshake between the sender, the receiver, and the dispatcher to efficiently transfer command and responsibility, consistent with the patient acuity score, for the patient from the sending location to the transport center, and wherein the updated one or more dashboards are concurrently displayed on the respective computing devices of the sender, receiver, and the dispatcher to provide the coordinated handshake;

receiving, by the MPTM, a real-time notification from the dispatcher that the patient has been delivered to the receiving location, and updating by the MPTM one or more dashboards, including the dispatcher dashboard, to provide a coordinated handshake between the sender, the receiver, and the dispatcher to efficiently transfer command and responsibility for the patient from the transport center to the receiving location; and closing the transport mission by the MPTM, wherein the patient is transported from the sending location to the receiving location, and wherein the updated one or more dashboards are concurrently displayed on the respective computing devices of the sender, receiver, and the dispatcher to provide the coordinated handshake.

2. The method of claim 1, further comprising, prior to receiving the inputted patient and transportation information by the acuity module, accessing, over the network, the acuity module using the sender computing device to display the interface providing the one or more input screens for inputting the patient and transportation information.

3. The method of claim 1, further comprising, prior to receiving, by the transport request module the acceptance response from the dispatcher, the transport request module receives a rejection response from the dispatcher, and the transport request module generates the transport request with an alternate receiving location.

4. The method of claim 1, wherein receiving by the MPTM a crew acknowledgement, comprises updating, by the MPTM, one or more dashboards of a crew computing device connected to the network at a transport base to display the crew assignment, and receiving, by the MPTM, a crew acknowledgement from the crew computing device.

5. The method of claim 1, wherein the appropriate vehicle and/or the one or more crew members assigned by the MPTM may be initially selected by the dispatcher by inputting the vehicle and/or the crew member information in a mission input screen displayed on the dispatch computing device.

6. The method of claim 1, wherein assigning, by the MPTM, the appropriate transport vehicle and optionally assigning the one or more crew members having the level of crew specialization specified in the transport plan, comprises use of a hard asset deployment module, and optionally a crew assignment module, respectively.

7. The method of claim 6, wherein assigning the transport vehicle by the hard asset deployment module, and optionally assigning the one or more crew members by the crew assignment module, comprises use of a vehicle profile dataset and a crew profile dataset, respectively.

8. The method of claim 7, wherein assigning the transport vehicle by the hard asset deployment module, and optionally assigning the one or more crew members by the crew assignment module, comprises use of the vehicle profile dataset and the crew profile dataset to calculate weight, balance, and fuel requirements.

9. The method of claim 1, wherein assigning, by the MPTM, the appropriate transport vehicle and optionally assigning the one or more crew members, comprises use of a weather evaluation module.

10. The method of claim 1, wherein assigning, by the MPTM, the appropriate transport vehicle and optionally assigning the one or more crew members, comprises consideration/optimization of one or more of resource availability, proximity, efficiency, cost, or reimbursement.

11. The method of claim 1, wherein assigning, by the MPTM, the appropriate transport vehicle and optionally assigning the one or more crew members, comprises assignment of a vehicle based on comparison of historical transport mission data between or among a plurality of transport bases.

12. The method of claim 1, wherein after transferring command and responsibility for the patient from the sending location to the transport center, and prior to receiving notification from the dispatcher that the patient has been delivered to the receiving location, the position of the transport vehicle is tracked by the MPTM to provide a vehicle location and an estimated time of arrival.

13. The method of claim 12, wherein during patient transport the MPTM updates one or more dashboards, including the dispatcher dashboard, with changes to the patient's condition based on input from the assigned crew.

14. The method of claim 12, wherein during patient transport the MPTM updates one or more dashboards, including the dispatcher dashboard, with the vehicle location and the estimated time of arrival, and/or updates an accessible vehicle position dataset.

15. The method of claim 1, wherein closing the transport mission by the MPTM, comprises prior receipt of a close instruction from the sender, the receiver, and/or the dispatcher.

16. The method of claim 1, comprising sending, by the MPTM, a mission summary to the sending and/or receiving locations.

17. The method of claim 1, wherein receiving, over the network by the AM, inputted patient and transportation information from the sender computing device, comprises receiving the patient and the transportation information from the receiver and/or the dispatcher.

18. The method of claim 1, wherein generating the acuity score and/or the transportation plan by the AM and/or converting the accepted transport request into the transport mission by the MPTM further comprises accessing one or more static or dynamic mission control datasets.

19. The method of claim 18, wherein the mission control data sets comprise one or more of a diagnosis-based protocol dataset, a vehicle profile dataset, a crew profile dataset, a hospital dataset, a weather dataset, an airport conditions dataset, or a vehicle position dataset.

20. The method of claim 1, wherein any computing device connected to the network for use in the method may be implemented as a computing device (12) or a mobile communication device (300).

21. A triaged patient transport method for use with a mission control computing device configured to execute and implement one or more application modules, and in operative communication over a network with a sender computing device, a dispatch computing device, and a receiver computing device, each operable to display one or more dashboards and/or input screens, and with one or more static or dynamic mission control datasets, the method comprising:

receiving, by a transport request module (TRM), patient and transportation information inputted from the sender computing device and/or from the dispatch computing device at a transport center, generating by the TRM a transport request that includes an acuity score and a transport plan, wherein the transport plan comprises a sending location, an appropriate receiving location, a mode of transportation, and a level of crew specialization, and wherein the acuity score is matched, independently or in unison, with the transportation mode, the crew specialization level, and the appropriate receiving location, updating by the TRM one or more dashboards, including a dispatcher dashboard on the dispatch computing device, with the transport request, and receiving, by the TRM, a receiver (receiving location) acceptance response for the transport request from the dispatch computing device;

converting, by a mission planning and tracking module (MPTM), the accepted transport request into a transport mission that assigns an appropriate vehicle to transport the patient, and that optionally assigns one or more crew members having the level of crew specialization specified in the transport plan, receiving by the MPTM a crew acknowledgement, receiving, by the MPTM, real-time indication that the patient has been picked up for transport, and updating by the MPTM one or more dashboards, including the dispatcher dashboard, to provide a coordinated handshake between the sender, the receiver and the dispatcher to efficiently transfer command and responsibility, consistent with the patient acuity score, for the patient from the sending location to the transport center, and wherein the updated one or more dashboards are concurrently displayed on the respective computing devices of the sender, receiver, and the dispatcher to provide the coordinated handshake;

receiving, by the MPTM, a real-time notification from the dispatcher that the patient has been delivered to the receiving location, and updating by the MPTM one or more dashboards, including the dispatcher dashboard, to provide a coordinated handshake between the sender, the receiver, and the dispatcher to efficiently transfer command and responsibility for the patient from the transport center to the receiving location; and closing the transport mission by the MPTM, wherein the patient is transported from the sending location to the receiving location, and wherein the updated one or more dashboards are concurrently displayed on the respective computing devices of the sender, receiver, and the dispatcher to provide the coordinated handshake.

22. The method of claim 21, further comprising, prior to receiving the inputted patient and transportation information by the TRM, accessing, over the network, the TRM using the dispatch computing device to display the interface providing the one or more input screens for inputting the patient and transportation information.

23. The method of claim 21, further comprising, prior to receiving, by the TRM, the acceptance response from the dispatcher, the TRM receives a rejection response from the dispatcher, and the TRM generates the transport request with an alternate receiving location.

24. The method of claim 21, wherein receiving by the MPTM a crew acknowledgement, comprises updating, by the MPTM, one or more dashboards of a crew computing device connected to the network at a transport base to display the crew assignment, and receiving, by the MPTM, a crew acknowledgement from the crew computing device.

25. The method of claim 21, wherein the appropriate vehicle and/or the one or more crew members assigned by the MPTM may be initially selected by the dispatcher by inputting the vehicle and/or the crew member information in a mission input screen displayed on the dispatch computing device.

26. The method of claim 21, wherein assigning, by the MPTM, the appropriate transport vehicle and optionally assigning the one or more crew members having the level of crew specialization specified in the transport plan, comprises use of a hard asset deployment module, and optionally a crew assignment module, respectively.

27. The method of claim 26, wherein assigning the transport vehicle by the hard asset deployment module, and optionally assigning the one or more crew members by the crew assignment module, comprises use of a vehicle profile dataset and a crew profile dataset, respectively.

28. The method of claim 27, wherein assigning the transport vehicle by the hard asset deployment module, and optionally assigning the one or more crew members by the crew assignment module, comprises use of the vehicle profile dataset and the crew profile dataset to calculate weight, balance, and fuel requirements.

29. The method of claim 21, wherein assigning, by the MPTM, the appropriate transport vehicle and optionally assigning the one or more crew members, comprises use of a weather evaluation module.

30. The method of claim 21, wherein assigning, by the MPTM, the appropriate transport vehicle and optionally assigning the one or more crew members, comprises consideration/optimization of one or more of resource availability, proximity, efficiency, cost, or reimbursement.

31. The method of claim 21, wherein assigning, by the MPTM, the appropriate transport vehicle and optionally assigning the one or more crew members, comprises assignment of a vehicle based on comparison of historical transport mission data between or among a plurality of transport bases.

32. The method of claim 21, wherein after transferring command and responsibility for the patient from the sending location to the transport center, and prior to receiving notification from the dispatcher that the patient has been delivered to the receiving location, the position of the transport vehicle is tracked by the MPTM to provide a vehicle location and an estimated time of arrival.

33. The method of claim 32, wherein during patient transport the MPTM updates one or more dashboards, including the dispatcher dashboard, with changes to the patient's condition based on input from the assigned crew.

34. The method of claim 32, wherein during patient transport the MPTM updates one or more dashboards, including the dispatcher dashboard, with the vehicle location and the estimated time of arrival, and/or updates an accessible vehicle position dataset.

35. The method of claim 21, wherein closing the transport mission by the MPTM, comprises prior receipt of a close instruction from the sender, the receiver, and/or the dispatcher.

36. The method of claim 21, comprising sending, by the MPTM, a mission summary to the sending and/or receiving locations.

37. The method of claim 21, wherein receiving, over a network by the TRM, inputted patient and transportation information, comprises receiving the patient and the transportation information from the receiver and/or the dispatcher.

38. The method of claim 21, wherein generating the transport request by the TRM and/or converting the accepted transport request into the transport mission by the MPTM further comprises accessing one or more static or dynamic mission control datasets.

39. The method of claim 38, wherein the mission control data sets comprise one or more of a diagnosis-based protocol dataset, a vehicle profile dataset, a crew profile dataset, a hospital dataset, a weather dataset, an airport conditions dataset, or a vehicle position dataset.

40. The method of claim 21, wherein any computing device connected to the network for use in the method may be implemented as a computing device (12) or a mobile communication device (300).

41. A system for triaging patients for transport from a sending location to a receiving location by matching patient acuity with transport and recipient resources over a network, comprising:
a sender computing device;
a dispatch computing device;
a receiver computing device;
one or more static or dynamic mission control datasets stored in memory; and
a mission control computing device, in operative communication over a network with the sender computing device, the dispatch computing device, and the datasets, and configured to execute and implement one or more application modules, including:
an acuity module (AM) operative to: display an interface providing one or more input screens on the sender computing device for inputting patient and transportation information by a sender; receive the inputted patient and transportation information; and generate a patient acuity score and a transportation plan, wherein the transportation plan comprises a sending location, a receiving location, a mode of transportation, and a level of crew specialization, and wherein in generating the transportation plan the acuity score is matched, independently or in unison, with the transportation mode, the level of crew specialization, and the receiving location;
a transport request module (MM) operative to: receive the acuity score and the transport plan from the AM; generate a transport request that includes the acuity score and the transport plan; update one or more dashboards, including a dispatcher dashboard displayed on the dispatch computing device at a transport center, with the transport request; and receive a receiver (receiving location) acceptance response for the transport request from a dispatcher; and
a mission planning and tracking module (MPTM) operative to: convert the accepted transport request into a transport mission that assigns an appropriate vehicle to transport the patient and optionally assigns one or more crew members having the level of crew specialization specified in the transport plan; receive real-time indication that the patient has been picked up for transport, and update one or more dashboards including the dispatcher dashboard to provide a coordinated handshake between the sender, the receiver and the dispatcher to efficiently transfer command and responsibility, consistent with the patient acuity score, for the patient from the sending location to the transport center; receive a real-time notification from the dispatcher that the patient has been delivered to the receiving location, and update one or more dashboards, including the dispatcher dashboard, to provide a coordinated handshake between the sender, the receiver and the dispatcher to efficiently transfer command and responsibility for the patient from the transport center to the receiving location; and close the transport mission, and wherein the updated one or more dashboards are concurrently displayed on the respective computing devices of the sender, receiver and the dispatcher to provide the coordinated handshakes.

42. The system of claim 41, further comprising a crew/base computing device, in each case operatively connected to the network.

43. The system of claim 42, wherein the system comprises a crew computing device, and wherein the MPTM is operative to update one or more dashboards of the crew computing device to display the crew assignment, and to receive a crew acknowledgement from the crew computing device.

44. The system of claim 41, wherein the system further comprises a hard asset deployment module, and/or a crew assignment module, and wherein the MPTM is operative with one or both of said modules in assigning the appropriate transport vehicle and optionally in assigning the one or more crew members.

45. The system of claim 44, wherein the hard asset deployment module and the crew assignment module are operative to access a vehicle profile dataset and/or a crew profile dataset to calculate one or more of weight, balance, or fuel requirements in assigning the transport vehicle and optionally in assigning the one or more crew members, respectively.

46. The system of claim 41, further comprising a weather evaluation module, and wherein the MPTM is operative to use the weather evaluation module in assigning the appropriate transport vehicle and optionally in assigning the one or more crew members.

47. The system of claim 41, wherein the MPTM is operative, during patient transport, to track the position of the transport vehicle to provide a vehicle location and an estimated time of arrival, to update one or more dashboards, including the dispatcher dashboard, with the vehicle location and the estimated time of arrival, and/or update an accessible vehicle position dataset, and/or to update one or more dashboards, including the dispatcher dashboard, with changes to the patient's condition based on input from the assigned crew.

48. The system of claim 41, wherein the AM, the MPTM, and/or the TRM are operative to access the one or more static or dynamic mission control datasets.

49. The system of claim 48, wherein the one or more mission control data sets comprises one or more of a diagnosis-based protocol dataset, a vehicle profile dataset, a crew profile dataset, a hospital dataset, a weather dataset, an airport conditions dataset, or a vehicle position dataset.

50. The system of claim 49, wherein the diagnosis-based protocol dataset comprises predetermined protocols for treating different medical conditions; wherein the vehicle profile dataset comprises information for one or more of fuel, speed, fuel consumption, or weight limits for each vehicle; wherein the crew profile dataset comprises weight and/or experience information each of the crew members; wherein the hospital dataset stores information about each hospital that may function as either the sending location or the receiving location; wherein the weather dataset stores information about the current weather; wherein the airport conditions dataset stores the condition of one or more airports that may be used to complete a transport mission; and wherein the vehicle position dataset stores positions of those vehicles currently conducting missions.

51. The system of claim 41, wherein any computing device connected to the network for use in the method may be implemented as a computing device (12) or a mobile communication device (300).

52. A non-transitory computer readable medium having stored thereon computer-executable instructions for performing the method according to claim 1.

53. A non-transitory computer readable medium having stored thereon computer-executable instructions for performing the method according to claim 21.

* * * * *